(12) United States Patent
Angibaud et al.

(10) Patent No.: US 7,067,531 B2
(45) Date of Patent: Jun. 27, 2006

(54) FARNESYL TRANSFERASE INHIBITING 6-HETEROCYCLYLMETHYL QUINOLINONE DERIVATIVES

(76) Inventors: Patrick René Angibaud, Janssen-Cilag S.A., 1, rue Camille Desmoulins, TSA 91003, F-92787 Issy-les-Moulineaux Cedex 9 (FR); Marc Gaston Venet, Janssen-Cilag S.A., 1, rue Camille Desmoulins, TSA 91003, F-92787 Issy-les-Moulineaux Cedex 9 (FR); Laurence Anne Mevellec, Janssen-Cilag S.A., 1, rue Camille Desmoulins, TSA 91003, F-92787 Issy-les-Moulineaux Cedex 9 (FR)

( * ) Notice: Subject to any disclaimer, the term of this patent is extended or adjusted under 35 U.S.C. 154(b) by 0 days.

(21) Appl. No.: 10/381,362

(22) PCT Filed: Sep. 18, 2001

(86) PCT No.: PCT/EP01/10975

§ 371 (c)(1),
(2), (4) Date: Mar. 24, 2003

(87) PCT Pub. No.: WO02/24687

PCT Pub. Date: Mar. 28, 2002

(65) Prior Publication Data

US 2003/0199547 A1   Oct. 23, 2003

(30) Foreign Application Priority Data

Sep. 25, 2000 (EP) .................... 00203368
Jun. 7, 2001 (EP) .................... 01202189

(51) Int. Cl.
*A61K 31/4704* (2006.01)
*C07D 401/14* (2006.01)

(52) U.S. Cl. .................... 514/312; 546/157
(58) Field of Classification Search ............ 514/312; 546/157
See application file for complete search history.

(56) References Cited

U.S. PATENT DOCUMENTS 6,037,350 A * 3/2000 Venet et al. .......... 514/312

FOREIGN PATENT DOCUMENTS

| EP | 0371564 B1 | 6/1990 |
| WO | WO 97/16443 A2 | 5/1997 |
| WO | 97/21701 * | 6/1997 |
| WO | WO 97/21701 A1 | 6/1997 |
| WO | WO 98/40383 A1 | 9/1998 |
| WO | WO 98/49157 A1 | 11/1998 |
| WO | 98/55124 * | 12/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |

OTHER PUBLICATIONS

Kohl et al., "Selective Inhibition of ras-Dependent Transformation by a Farnesyltransferase Inhibitor." *Science*, 1993, pp. 1934-1937, vol. 260, No. 5116.

Rak et al., "Mutant ras Oncogenes Upregulate VEGF/VPF Expression: Implications for Induction and Inhibition of Tumor Angiogenesis." *Cancer Research*, 1995, pp. 4575-4580, vol. 55, No. 20.

* cited by examiner

*Primary Examiner*—Patricia L. Morris

(57) ABSTRACT

This invention comprises the novel compounds of formula (I)

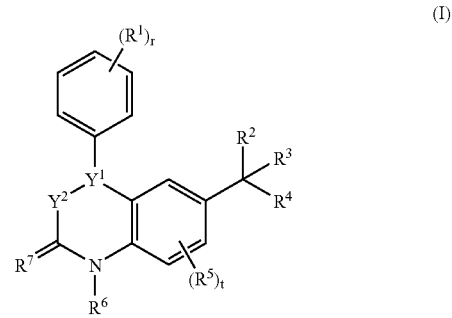

wherein r, t, $Y^1$—$Y^2$, $R^1$, $R^2$, $R^3$, $R^4$, $R^5$, $R^6$ and $R^7$ have defined meanings, having farnesyl transferase inhibiting activity; their preparation, compositions containing them and their use as a medicine.

12 Claims, No Drawings

FARNESYL TRANSFERASE INHIBITING 6-HETEROCYCLYLMETHYL QUINOLINONE DERIVATIVES

CROSS REFERENCE TO RELATED APPLICATIONS

This application is the national stage of Application No. PCT/EP01/10975, filed Sep. 18, 2001 which application claims priority from EP 00203368.6 filed Sep. 25, 2000, and EP 01202189.5 filed Jun. 7, 2001.

The present invention is concerned with novel 6-heterocyclylmethyl quinolinone derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., *Science*, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolinone and quinazolinone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499 and 00/47574.

Unexpectedly, it has been found that the present novel 6-heterocyclylmethyl quinolinones compounds show farnesyl protein transferase inhibiting activity.

The present invention concerns compounds of formula (I):

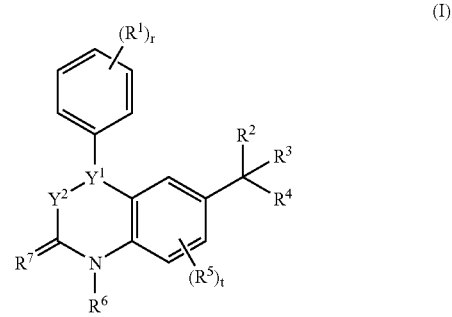

or a pharmaceutically acceptable salt or N-oxide or stereochemically isomeric form thereof, wherein
r is 0, 1, 2, 3, 4 or 5;
t is 0, 1, 2 or 3;
$>Y^1-Y^2-$ is a trivalent radical of formula

 (y-2)

 (y-4)

wherein $R^9$ is hydrogen, halo, cyano, $C_{1-6}$alkyl, hydroxy$C_{1-6}$alkyl, $C_{1-6}$alkyloxy$C_{1-6}$alkyl, —$(CR^{20}R^{21})_p$—$C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alkyloxycarbonyl, aryl or a group of formula —$NR^{22}R^{23}$, —$C_{1-6}$alkyl-$NR^{22}R^{23}$, —$C_{2-6}$alkenyl-$NR^{22}R^{23}$, —$CONR^{22}R^{23}$ or —$NR^{22}$—$C_{1-6}$alkyl-$NR^{22}R^{23}$;

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or —$(CR^{20}R^{21})_p$—$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, $OCF_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;

$R^1$ is azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}S$ $C_{1-6}$alkyl, trihalomethyl, aryl$C_{1-6}$alkyl, $Het^2C_{1-6}$alkyl, —$C_{1-6}$alkyl-$NR^{22}R^{23}$, —$C_{1-6}$alkyl$NR^{22}C_{1-6}$alkyl-$NR^{22}R^{23}$, —$C_{1-6}$alkyl$NR^{22}COC_{1-6}$alkyl, —$C_{1-6}$alkyl$NR^{22}COAlkAr^2$, —$C_{1-6}$alkyl$NR^{22}COAr^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, —$OC_{1-6}$alkyl-$NR^{22}R^{23}$, trihalomethoxy, aryl$C_{1-6}$alkyloxy, $Het^2C_{1-6}$alkyloxy, $C_{1-6}$alkylthio, $C_{2-6}$alkenyl, cyano$C_{2-6}$alkenyl, —$C_{2-6}$alkenyl-$NR^{22}R^{23}$, hydroxycarbonyl$C_{2-6}$alkenyl, $C_{1-6}$alkyloxycarbonyl-C$_{2-6}$alkenyl, C$_{2-6}$alkynyl, —CHO, C$_{1-6}$alkylcarbonyl, hydroxyC$_{1-6}$alkylcarbonyl, hydroxycarbonyl, C$_{1-6}$alkyloxycarbonyl, —CONR$^{22}$R$^{23}$, —CONR$^{22}$—C$_{1-6}$alkyl-Het$^2$, —CONR$^{22}$—C$_{1-6}$ alkyl-Het$^2$, —CONR$^{22}$—C$_{1-6}$alkyl-Ar$^2$, —CONR$^{22}$—O—C$_{1-6}$alkyl, —CONR$^{22}$—C$_{1-6}$alkenyl, —NR$^{22}$R$^{23}$, —OC(O)R$^{24}$, —CR$^{24}$=NR$^{25}$, —CR$^{24}$=N—OR$^{25}$, —NR$^{24}$C(O) NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, aryloxy, Het$^2$-oxy, or a group of formula -Z, —CO-Z or —CO—NR$^y$-Z in which R$^y$ is hydrogen or C$_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, C$_{1-6}$alkylthio, hydroxy, —NR$^{22}$R$^{23}$, C$_{1-6}$alkylsulphonylamino, C$_{1-6}$alkyl, haloC$_{1-6}$alkyl, C$_{1-6}$alkyloxy or phenyl; or two R$^1$ substituents adjacent to one another on the phenyl ring may form together a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

—CH=CH—CH=CH— (a-6)

R$^{24}$ and R$^{25}$ are independently hydrogen, C$_{1-6}$ alkyl, —(CR$_{20}$R$_{21}$)p—C$_{3-10}$cycloalkyl or arylC$_{1-6}$alkyl;

R$^{26}$, R$^{27}$ and R$^{28}$ are independently hydrogen and C$_{1-6}$alkyl or C(O) C$_{1-6}$alkyl;

R$^2$ is a mono- or bi-cyclic heterocyclic ring containing either at least one oxygen heteroatom or two or more heteroatoms selected from oxygen, sulphur and nitrogen, each such ring being optionally substituted by one or two substituents each independently selected from halo, cyano, hydroxy, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$, C$_{1-6}$alkylsulfonylamino, oxime, phenyl or benzyl;

R$^3$ is hydrogen, halo, cyano, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, arylC$_{1-6}$alkyloxyC$_{1-6}$alkyl, C$_{1-6}$alkylthioC$_{1-6}$alkyl, hydroxycarbonylC$_{1-6}$alkyl, C$_{1-6}$alkylcarbonylC$_{1-6}$alkyl, C$_{1-6}$alkyloxycarbonylC$_{1-6}$alkyl, —C$_{1-6}$alkyl-NR$^{22}$R$^{23}$, —C$_{1-6}$alkyl-CONR$^{22}$R$^{23}$, arylC$_{1-6}$alkyl, Het$^2$C$_{1-6}$alkyl, C$_{2-6}$alkenyl, —C$_{2-6}$alkenylNR$^{22}$R$^{23}$, C$_{2-6}$alkynyl, hydroxycarbonyl, C$_{1-6}$alkyloxycarbonyl, aryl, or Het$^2$; or a radical of formula

| —O—R$^{10}$ | (b-1) |
| —S—R$^{10}$ | (b-2) or |
| —NR$^{11}$R$^{12}$ | (b-3) | wherein R$^{10}$ is hydrogen, C$_{1-6}$alkyl, —(CR$^{20}$R$^{21}$)$_p$—C$_{3-10}$cycloalkyl, arylC$_{1-6}$alkyl, C$_{2-6}$alkenyl, C$_{2-6}$alkynyl, C$_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula —Alk-OR$^{13}$ or -Alk-NR$^{14}$R$^{15}$;

R$^{11}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkylcarbonylC$_{1-6}$alkyl, arylC$_{1-6}$ alkyl, C$_{2-6}$alkenyl, C$_{2-6}$alkynyl, aryl, C$_{1-6}$alkyloxy, a group of formula —NR$^{22}$R$^{23}$, C$_{1-6}$alkylcarbonylamino, C$_{1-6}$alkylcarbonyl, haloC$_{1-6}$ alkylcarbonyl, arylC$_{1-6}$alkylcarbonyl, Het$^2$C$_{1-6}$alkylcarbonyl, arylcarbonyl, C$_{1-6}$alkyloxycarbonyl, C$_{1-6}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl andC$_{1-6}$alkyloxycarbonyl substiuents; aminocarbonylcarbonyl, mono- or di(C$_{1-6}$di(C$_{1-6}$alkyl)aminoC$_{1-6}$alkylcarbonyl, or a radical of formula -Alk-OR$^{13}$ or Alk-NR$^{14}$R$^{15}$;

wherein Alk is C$_{1-6}$alkanediyl;

R$^{13}$ is hydrogen, C$_{1-6}$alkyl, —(CR$^{20}$R$^{21}$)$_p$—C$_{3-10}$cycloalkyl , C$_{2-6}$alkenyl, C$_{2-6}$alkynyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{15}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, aryl or arylC$_{1-6}$alkyl;

R$^4$ is a radical of formula

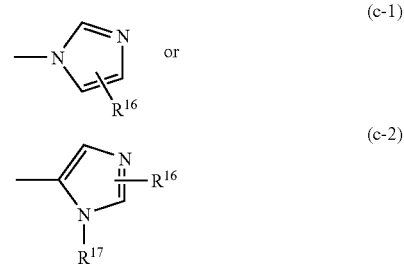

wherein R$^{16}$ is hydrogen, halo, C$_{1-6}$alkyl, —(Cr$^{20}$R$^{21}$)$_p$—C$_{3-10}$cycloalkyl, hydroxyC$_{1-6}$alkyl, C$_{1-6}$alkyloxyC$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, hydroxycarbonyl, C$_{1-6}$alkyloxycarbonyl or aryl, R$^{17}$ is hydrogen, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylC$_{1-6}$alkyl, C$_{1-6}$alkyloxycarbonylC$_{1-6}$alkyl, mono- or di(C$_{1-6}$alkyl)aminosulphonyl or —C$_{1-6}$alkylP(O)OR$^{24}$OR$^{25}$;

R$^5$ is cyano, hydroxy, halo, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkyloxy, arylC$_{1-6}$alkyloxy, Het$^2$C$_{1-6}$alkyloxy, hydroxycarbonyl, C$_{1-6}$alkyloxycarbonyl, or a group of formula —NR$^{22}$R$^{23}$ or —CONR$^{22}$R$^{23}$;

R$^6$ is hydrogen, C$_{1-6}$alkyl, —(CR$^{20}$R$^{21}$)$_p$—C$_{3-10}$cycloalkyl, cyanoC$_{1-6}$alkyl, —C$_{1-6}$alkylCO$_2$R$^{24}$, aminocarbonylC$_{1-6}$alkyl or —C$_{1-6}$alkyl-NR$^{22}$R$^{23}$, $R^{24}SO_2$, $R^{24}SO_2C_{1-6}$alkyl, $—C_{1-6}$alkyl-$OR^{24}$, $—C_{1-6}$alkyl-$SR^{24}$, $—C_{1-6}$alkyl$CONR^{22}—C_{1-6}$alkyl-$NR^{22}R^{23}$, $—C_{1-6}$alkyl$CONR^{22}—C_{1-6}$alkyl-$Het^2$, $—C_{1-6}$alkyl$CONR^{22}—C_{1-6}$alkyl-$Ar^2$, $—C_{1-6}$alkyl $CONR^{22}$-$Het^2$, $—C_{1-6}$alkyl$CONR^{22}Ar^2$, $—C_{1-6}$alkyl$CONR^{22}—O—C_1$alkyl, $—C_{1-6}$alkyl-$CONR^{22}—C_{1-6}$alkenyl, -Alk-$Ar^2$ or -Alk$Het^2$;

$R^7$ is oxygen or sulphur;

$Ar^2$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkyl$NR^{22}R^{23}$, $C_{1-6}$alyloxy, $OCF_3$, hydroxycarbonyl, $C_{1-6}$alkyloxycarbonyl, aryloxy, $—NR^{22}R^{23}$, $C_{1-6}$alkylsulfonylamino, oxime or phenyl, or a bivalent substituent of formula $—O—CH_2—O—$ or $—O—CH_2—CH_2—O—$;

$Het^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkyl$NR^{22}R^{23}$, $C_{1-6}$alkyloxy, $OCF_3$, hydroxycarbonyl, $C_{1-6}$alkyloxycarbonyl, $—CONR^{22}R^{23}$, $—NR^{22}R^{23}$, $C_{1-6}$alkylsulfonylamino, oxime or phenyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, $C_{1-6}$alkyl, $C_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

Examples of compounds of formula (I) include those wherein one or more of the following restrictions apply:

r is 0, 1 or 2;

t is 0 or 1;

>$Y^1$–$Y^2$— is a trivalent radical of formula

>$C=CR^9$— (y-2)

wherein $R^9$ is hydrogen, cyano, halo, $C_{1-6}$alkyl, hydroxy$C_{1-6}$alkyl, hydroxycarbonyl or aminocarbonyl;

$R^1$ is halo, $C_{1-6}$alkyl, $—(CR^{20}R^{21})_p$—$C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$alkylthio, hydroxycarbonyl, $C_{1-6}$alkyloxycarbonyl, $—CONR^{22}R^{23}$, or $—CH=NOR^{25}$; or two $R^1$ substituents adjacent to one another on the phenyl ring may independently form together a bivalent radical of formula $—O—CH_2—O—$ (a-1)

$—O—CH_2—CH_2—O—$ (a-2)

$R^2$ is a 5- or 6-membered monocyclic heterocyclic ring containing either one oxygen heteroatom or two or three heteroatoms selected from oxygen, sulphur and or nitrogen or a 9- or 10-membered bicyclic heterocyclic ring containing either one oxygen heteroatom or two or three heteroatoms selected from oxygen, sulphur and or nitrogen $R^3$ is hydrogen, $C_{1-6}$alkyl, $—(CR^{20}R^{21})_p$—$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, $—C_{1-6}$alkyl $NR^{22}R^{23}$, $Het^2C_{1-6}$alkyl, $—C_{2-6}$alkenyl $NR^{22}R^{23}$, or -$Het^2$; or a group of formula $—O—R^{10}$ (b-1)

$—NR^{11}R^{12}$ (b-3)

wherein $R^{10}$ is hydrogen, $C_{1-6}$alkyl, or $—(CR^{20}R^{21})_p$—$C_{3-10}$cycloalkyl, or a group of formula -Alk-$OR^{13}$or -Alk-$NR^{14}R^{15}$;

$R^{11}$ is hydrogen or $C_{1-6}$alkyl;

$R^{12}$ is hydrogen, hydroxy, $C_{1-6}$alkyl, —$(CR^{20}R^{21})_p$—$C_{3-10}$cycloalkyl, $C_{1-6}$alkyloxy, $C_{1-6}$alkylcarbonyl, aminocarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl or —$(CR^{20}R^{21})_p$—$C_{3-10}$cycloalkyl;

$R^{14}$ is hydrogen, $C_{1-6}$alkyl, or —$(CR^{20}R^{21})_p$—$C_{3-10}$cycloalkyl;

$R^{15}$ is hydrogen or $C_{1-6}$alkyl;

$R^4$ is a radical of formula (c-2)

wherein $R^{16}$ is hydrogen, halo or $C_{1-6}$alkyl, $R^{17}$ is hydrogen, $C_{1-6}$alkyl, —$(CR^{20}R^{21})_p$—$C_{3-10}$cycloalkyl, $C_{1-6}$alkyloxy$C_{1-6}$alkyl or trifluoromethyl;

$R^5$ is cyano, halo, $C_{1-6}$alkyl, $C_{2-6}$alkynyl, $C_{1-6}$alkyloxy or $C_{1-6}$alkyloxycarbonyl:

$R^6$ is hydrogen, $C_{1-6}$alkyl, —$C_{1-6}$alkylCO$_2$R$^{24}$, —$C_{1-6}$alkyl-C(O)NR$^{22}$R$^{23}$, -Alk-Ar$^2$, -AlkHet$^2$ or —$(CR^{20}R^{21})_p$—$C_{3-10}$cycloalkyl, $R^7$ is oxygen; Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:

>Y$^1$–Y$^2$— is a trivalent radical of formula (y-2), wherein $R^9$ is hydrogen, halo, $C_{1-4}$alkyl, hydroxycarbonyl, or $C_{1-4}$alkyloxycarbonyl;

r is 0, 1 or 2;

t is 0;

$R^1$ is halo, $C_{1-6}$alkyl or two $R^1$ substituents ortho to one another on the phenyl ring may independently form together a bivalent radical of formula (a-1);

$R^2$ is a 5- or 6-membered monocyclic heterocyclic ring containing one oxygen heteroatom or two heteroatoms selected from oxygen, sulphur or nitrogen or a 9- or 10-membered bicyclic heterocyclic ring in which a benzene ring is fused to a heterocyclic ring containing either at least one oxygen heteroatom or two or heteroatoms selected from oxygen, sulphur or nitrogen, optionally substituted by halo, cyano, $C_{1-6}$alkyl or aryl;

$R^3$ is Het$^2$ or a group of formula (b-1) or (b-3) wherein $R^{10}$ is hydrogen or a group of formula -Alk-OR$^{13}$.

$R^{11}$ is hydrogen;

$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;

Alk is $C_{1-6}$alkanediyl and $R^{13}$ is hydrogen;

$R^4$ is a group of formula (c-2) wherein $R^{16}$ is hydrogen, halo or mono- or di($C_{1-4}$alkyl)amino;

$R^{17}$ is hydrogen or $C_{1-6}$alkyl;

$R^6$ is —$(CR^{20}R^{21})_p$—$C_{3-10}$cycloalkyl, —$C_{1-6}$alkylCO$_2$R$^{24}$, aminocarbonyl$C_{1-6}$alkyl, -Alk-Ar$^2$ or -AlkHet$^2$ or $C_{1-6}$alkyl;

$R^7$ is oxygen;

aryl is phenyl.

A particular group of compounds consists of those compounds of formula (I) wherein >Y$^1$–Y$^2$ is a trivalent radical of formula (y-2), r is 0 or 1, t is 0, $R^1$ is halo, $C_{(1-4)}$alkyl or forms a bivalent radical of formula (a-1), $R^2$ is a 5- or 6-membered monocyclic heterocyclic ring containing either one oxygen heteroatom or two heteroatoms selected from oxygen, sulphur or nitrogen or a 9- or 10-membered bicyclic heterocyclic ring in which a benzene ring is fused to a heterocyclic ring containing either one oxygen heteroatom or two or heteroatoms selected from oxygen, sulphur or nitrogen, optionally substituted by halo, cyano, $C_{1-6}$alkyl or aryl; $R^3$ is hydrogen or a radical of formula (b-1) or (b-3), $R^4$ is a radical of formula (c-2), $R^{10}$ is hydrogen or -Alk-OR$^{13}$, $R^{12}$ is hydrogen and $R^{12}$ is hydrogen or $C_1$-$C_{1-6}$alkylcarbonyl and $R^{13}$ is hydrogen; $R^6$ is $C_{1-6}$alkyl, —CH$_2$—$C_{3-10}$cycloalkyl, —$C_{1-6}$alkylCO$_2$R$^{24}$ (wherein R$^{24}$ is hydrogen or ethyl), aminocarbonyl$C_{1-6}$alkyl, -Alk-Ar$^2$ or -AlkHet$^2$; and $R^7$ is oxygen.

More preferred compounds are those compounds of formula (I) wherein >Y$^1$–Y$^2$ is a trivalent radical of formula (y-2), r is 0 or 1, s is 1, t is 0, $R^1$ is halo, preferably chloro and most preferably 3-chloro, $R^2$ is a furyl, diazolyl, oxazolyl or benzodiazolyl, benzotriazolyl group, optionally substituted by halo preferably chloro, cyano, $C_{1-6}$alkyl, preferably methyl or aryl; $R^3$ is hydrogen or a radical of formula (b-1) or (b-3), $R^4$ is a radical of formula (c-2), $R^9$ is hydrogen, $R^{10}$ is hydrogen, $R^{11}$ is hydrogen and $R^{12}$ is hydrogen $R^6$ is $C_{1-6}$alkyl, —CH$_2$—$C_{3-10}$cycloalkyl or —$C_{1-6}$ alkylAr$^2$; $R^7$ is oxygen.

Especially preferred compounds are those compounds of formula (I) wherein >Y$^1$–Y$^2$ is a trivalent radical of formula (y-2), r is 1, t is 0, $R^1$ is halo, preferably chloro, and most preferably 3-chloro, $R^2$ is a 3-furyl, imidazol-1-yl, , benzimidazol-1-yl group optionally substituted by halo preferably chloro, cyano, $C_{1-6}$alkyl, preferably methyl or phenyl; $R^3$ is a radical of formula (b-1) or (b-3), $R^4$ is a radical of formula (c-2), $R^9$ is hydrogen, $R^{10}$ and $R^{11}$ are hydrogen and $R^{12}$ is hydrogen or hydroxy, $R^6$ is $C_{1-6}$alkyl, —CH$_2$—$C_{3-10}$cycloalkyl or -alkylAr$^2$; and $R^7$ is oxygen.

The most preferred compounds according to the invention are:

(±)-4-(3-chlorophenyl)-6-[3-furanylhydroxy(1-methyl-1H-imidazol-5-yl)methyl]-1-methyl-2(1H)-quinolinone, (±)-6-[amino-3-furanyl(1-methyl-1H-imidazol-5-yl)methyl]-4-(3-chlorophenyl)-1-methyl-2(1H)-quinolinone, 6-[1H-benzimidazol-1-yl(1-methyl-1H-inidazol-5-yl)methyl]-4-(3-chlorophenyl)-1-methyl-2(1H)-quinolinone, 6-[1H-1,2,3-benzotriazol-1-yl(1-methyl-1H-imidazol-5-yl)methyl]-4-(3-chlorophenyl)-1-methyl-2(1H)-quinolinone, 4-(3-chlorophenyl)-1-methyl-6-[(1-methyl-1H-imidazol-5-yl)(2-phenyl-1H-imidazol-1-yl)methyl]-2(1H)-quinolinone, 4-(3-chlorophenyl)-6-[(2-ethyl-1H-imidazol-1-yl)(1-methyl-1H-imidazol-5-yl)methyl]-1-methyl-2(1H)-quinolinone, 4-(3-chlorophenyl)-1-methyl-6-[(1-methyl-1H-imidazol-5-yl)(4-methyl-1H-imidazol-1-yl)methyl]-2(1H)-quinolinone, and their pharmaceutically acceptable salts.

The compounds of formula (I) and their pharmaceutically acceptable salts and N-oxides and stereochemically isomeric forms thereof may be prepared in conventional manner, for example by a process which comprises:

a) cyclising a compound of formula (II)

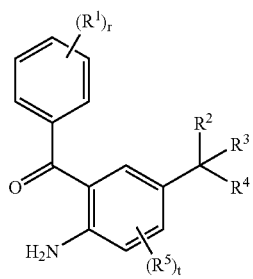

with a reagent serving to form a compound of formula (I) in which $R^6$ is hydrogen and $R^7$ is oxygen;

b) reacting a compound of formula (III):

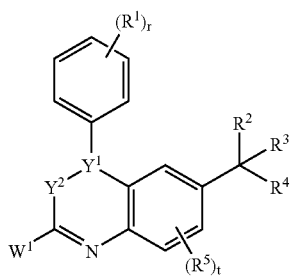

in which $W^1$ represents a replaceable or reactive group, with a reagent serving either to react with or replace the $W^1$ group in compound (III) to form a compound of formula (I) in which $R^6$ is hydrogen and $R^7$ is an oxygen or sulphur group; or c) reacting a compound of formula (IV):

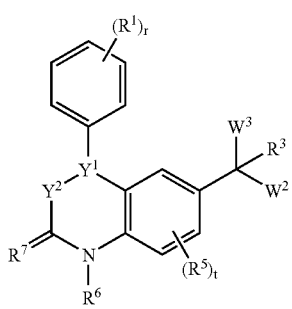

in which $W^2$ is a leaving group and $W^3$ is the group $R^2$ above or $W^2$ is the group $R^4$ above and $W^3$ is a leaving group, with a reagent serving to replace the leaving group $W^2$ or $W^3$ with the respective $R^4$ or $R^2$ group; or d) reacting a compound of formula (V):

(V)

(in which $R^x$ is the group $R^2$ or $R^4$ above) with a heterocyclic reagent of formula $R^{4a}L$ (when $R^x$ is $R^2$) or $R^{2a}L$ (when $R^x$ is $R^4$) in which L is a leaving atom or group and $R^{2a}$ is $R^2$ or a precursor group therefor and $R^{4a}$ is $R^4$ or a precursor group therefor, and if required, converting said precursor group to the parent group, to form a compound of formula (I) in which $R^3$ is hydroxy;

e) reacting a compound of formula (VI):

(VI)

with a reagent serving to convert the said compound (VI) to a compound of formula (I) in which $R^6$ is hydrogen and $R^7$ is oxygen;

and optionally effecting one or more of the following conversions in any desired order:
 (i) converting a compound of formula (I) into a different compound of formula (I);
 (ii) converting a compound of formula (I) in to a pharmaceutically acceptable salt or N-oxide thereof;
 (iii) converting a pharmaceutically acceptable salt or N-oxide of a compound of formula (I) into the parent compound of formula (I);
 (iv) preparing a stereocherical isomeric form of a compound of formula (I) or a pharmaceutically acceptable salt or N-oxide thereof.

With regard to process a), this can be effected as described for example in an analogous manner to that described in WO 97/21701 and WO98/49157 referred to above. Thus, the cyclisation may be effected for example by subjecting the compound of formula (II) to an acetylation reaction, e.g. by treatment with the anhydride of a carboxylic acid, e.g. acetic anhydride in a reaction-inert solvent, e.g. toluene, and subsequent reaction with a base such as potassium tert-butoxide in a reaction-inert solvent such as 1,2-dimethoxyethane.

With regard to process b), this can also be effected for example in an analogous manner to that as described in WO 97/21701 and WO98/49157 referred to above for the preparation of compounds in which $R^7$ is oxygen, for example by hydrolysis of an ether of formula (II) in which $W^1$ is $C_{1-6}$alkyloxy in an aqueous acid solution such hydrochloric acid Alternatively a compound of formula (III) in which $W^1$ is a chloro radical can be used.

With regard to process c), this can be effected for example by N-alkylating an intermediate of formula (IVa), wherein $W^2$ is an appropriate leaving group such as, for example, chloro, bromo, methanesulfonyloxy or benzenesulfonyloxy, with an intermediate of formula (VII) to form a compound of formula (I) in which $R^4$ is a group of formula (c-1) represented by compounds of formula (I-a):

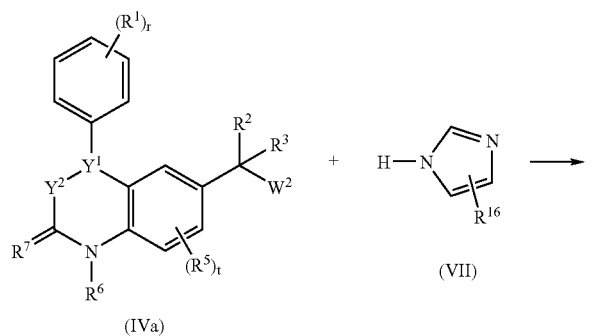

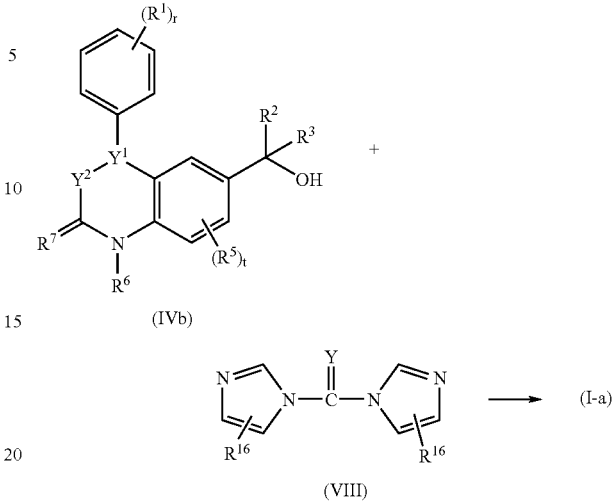

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

Similar procedures can be used to introduce the $R^2$ group using a compound of formula (IV) in which $W^3$ is a leaving group.

With regard to process d), this can be used to introduce the $R^4$ group, for example by reacting a compound of formula (V) in which $R^x$ is $R^2$ with an imidazole reagent to form a compound of formula (I) in which $R^4$ is a group of formula (c-2). In more detail, the compounds of formula (I) wherein $R^4$ represents a radical of formula (c-2), $R^3$ is hydroxy and R is $C_{1-6}$alkyl, said compounds being referred to as compounds of formula (I-b-1) may be prepared by reacting an intermediate ketone of formula (Va) with an intermediate of formula (III-1). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogous to silane derivatives can also be applied.

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (IVb) in which $W^2$ is hydroxy with an intermediate of formula (VIII), wherein Y is oxygen or sulfur, such as, for example, a 1,1'-carbonyldiimidazole.

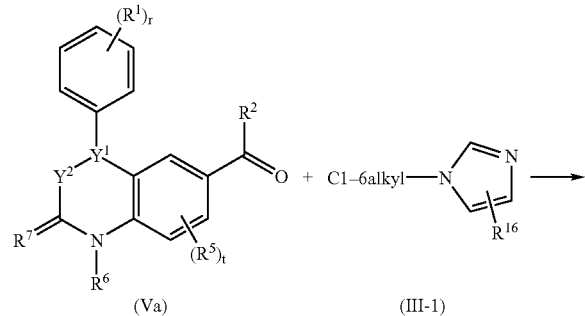

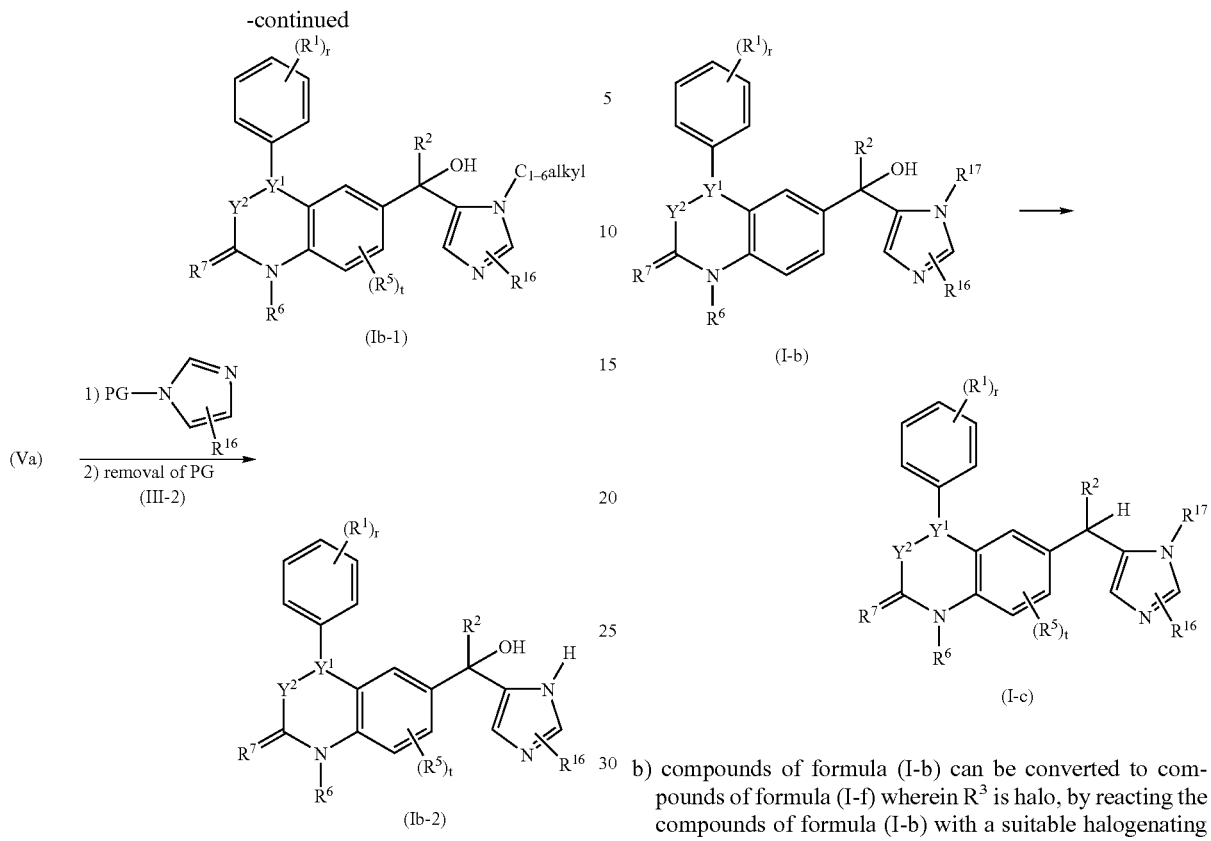

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (Va) with a intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2). Similar procedures can be used to introduce the $R^2$ group by reacting a compound of formula (V) in which $R^x$ is $R^4$ with a $R^2L$ reagent for example a lithium compound.

With regard to process e), this may be effected for example as described in WO 97/21701 referred to above, by reacting the nitrone of formula (VI) with the anhydride of a carboxylic acid, e.g. acetic anhydride, thus forming the corresponding ester on the 2-position of the quinoline moiety, which ester can then be hydrolysed in situ to the corresponding quinolinone using a base such potassium carbonate.

Examples of the interconversion of one compound of formula (I) into a different compound of formula (I) include the following reactions:

a) compounds of formula (I-b) can be converted to compounds of formula (I-c), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula $H-NR^{11}R^{12}$ in a reaction-inert solvent, thereby yielding compounds of formula (I-g).

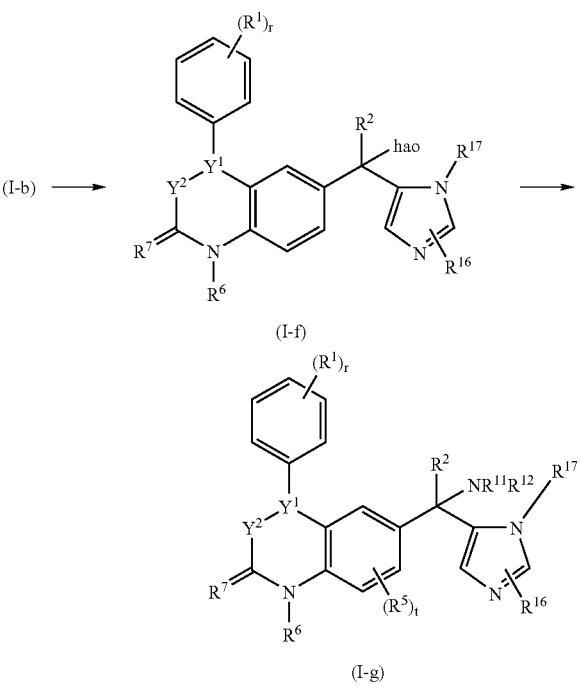

c) compounds of formula (I-b) can be converted into compounds of formula (I-g) for example by treatment with SOCl$_2$, and then NH$_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with SnCl$_2$ in the presence of concentrated HCl in acetic acid at reflux;

e) compounds of formula (I) in which >Y$^1$–Y$^2$ represents a radical of formula or (y-2) can be converted into corresponding compounds of formula (I) in which >Y$^1$–Y$^2$ represents a radical of formula (y-4) respectively, by conventional reduction procedures for example hydrogenation.

f) compounds of formula (I) in which X is oxygen can be converted into corresponding compounds of formula (I) in which X is sulphur with a reagent such as phosphorus pentasulfide or Lawesson's reagent in a suitable solvent such as, for example, pyridine.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

The intermediates and starting materials used in the above-described processes my be prepared in conventional manner using procedures known in the art for example as described in the above -mentioned patent specifications WO 97/16443, WO 97/21701, WO 98/40383, WO 98/49157 and WO 00/39082.

Compounds of formula (III) in which W$^1$ is chloro or more preferably OCH$_3$, R$^3$ is hydroxy and Y$^1$–Y$^2$ is (y-2), herein referred to as compounds of formula (IIIa), may be prepared for example by procedures summarised in the following synthetic Routes A and B:

Route A

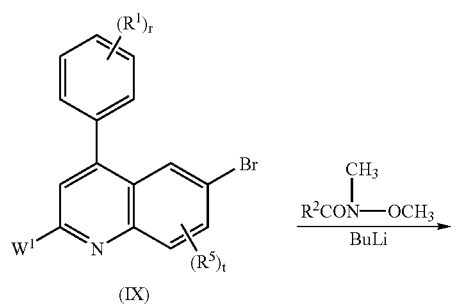

(IX)

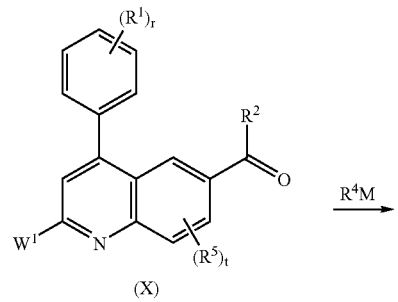

(X)

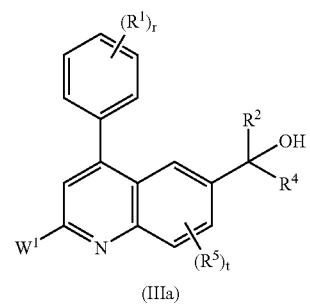

(IIIa)

Route B

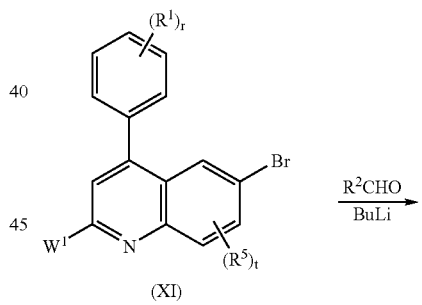

(XI)

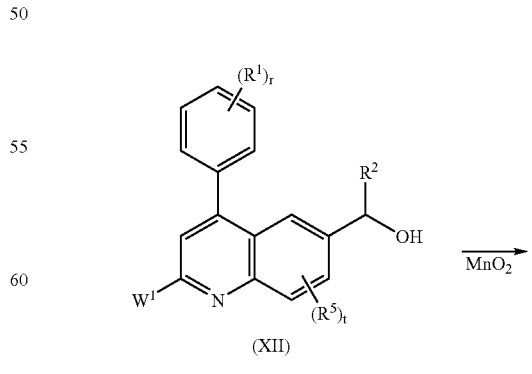

(XII)

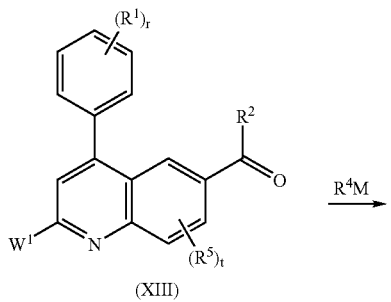

(XIII)

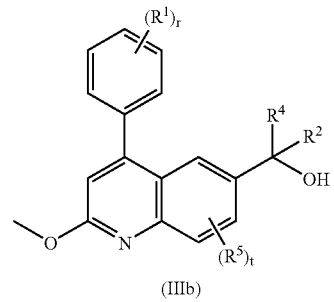

(IIIb)

Compounds of formula (V) in which $R^x$ is $R^4$ $R^7$ is oxygen and $Y^1-Y^2$ is (y-2), herein referred to as compounds of formula (Vb), may be prepared for example by procedures summarised in the following synthetic Route D:

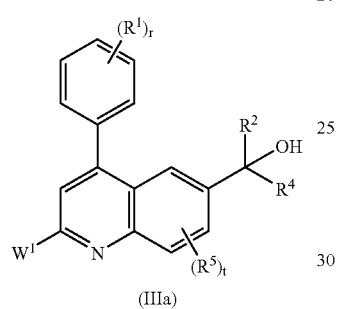

(IIIa)

Compounds of formula (III) in which $W^1$ is $OCH_3$, $R^3$ is hydroxy, and $Y^1-Y^2$ is (y-2), herein referred to as compounds of formula (IIIb), may be prepared for example by procedures summarised in the following synthetic Route C:

Route D

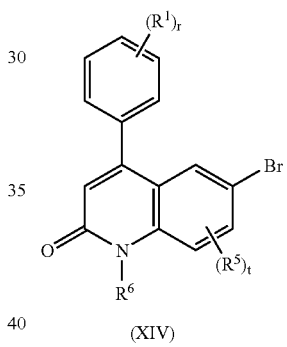

(XIV)

Route C

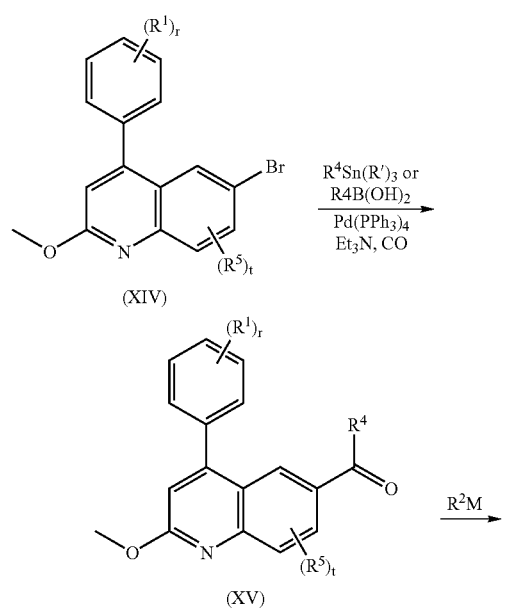

(XIV)

(XV)

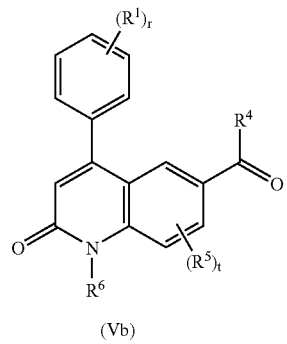

(Vb)

Compounds of formula (IV) in which $W^2$ is Cl, $W^3$ is $R^4$, $R^7$ is oxygen, $R^3$ is H and $Y^1-Y^2$ is (y-2), herein referred to as compounds of formula (IVc), may be prepared for example by procedures summarized in the following reaction scheme E:

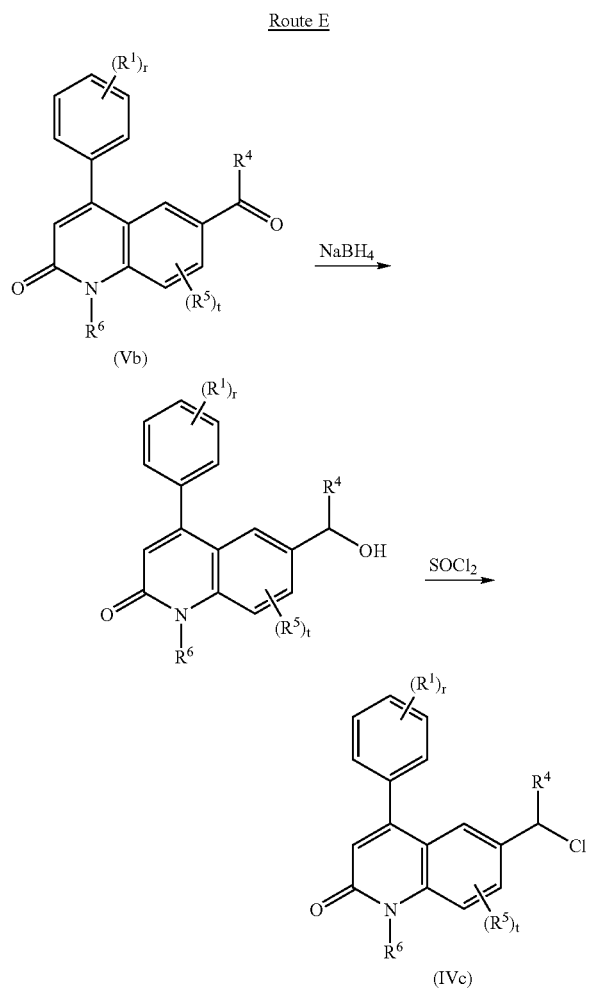

Route E (Vb)

(IVc)

In general in relation to the above Routes A, B and C, the groups $R^2$ and $R^4$ can be interchanged, for example, where a $R^2$ reagent is used to introduce the $R^2$ group, the corresponding $R^4$ reagent can alternatively be employed to introduce the $R^4$ group. Thus, when a $R^2$ reagent is used to introduce the $R^2$ group before the $R^4$ group, it is possible in the alternative to use the corresponding $R^4$ reagent to introduce the $R^4$ group before the $R^2$ group.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes, may be inhibited by the compounds of this invention.

The compound according to the invention can be used for other therapeutic purposes, for example:

a) the sensitisation of tumors to radiotherapy by administering the compound according to the invention before, during or after irradiation of the tumor for treating cancer, for example as described in WO 00/01411;
b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;
c) inhibiting smooth muscle cell proliferation including vascular proliferative disorders, atherosclerosis and restenosis, for example as described in WO 98/55124;
d) treating inflammatory conditions such as ulcerative colitis, crohn's disease, allergic rhinitis, graft vs host disease, conjunctivitis, asthma, ards, behcets disease, transplant rejection, uticaria, allergic dermatitis, alopecia areata, scleroderma, exanthem, eczema, dermatomyositis, acne, diabetes, systemic lupus erythematosis, kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;
h) inhibiting viral morphogenesis for example by inhibiting the prenylation or the post-prenylation reactions of a viral protein such as the large delta antigen of hepatitis D virus; and the treatment of HIV infections;
i) treating polycystic kidney disease;
j) suppressing induction of inducible nitric oxide including nitric oxide or cytokine mediated disorders, septic shock, inhibiting apoptosis and inhibiting nitric oxide cytotoxicity;
k) treating malaria.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, antitumor anthracycline derivatives for example daunorubicin, doxorubicin or idarubicin; HER2 antibodies for example trastzumab; and anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment is may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

Experimental Part

Hereinafter "THF" means tetrahydrofuran, "DIPE" means diisopropyl ether, "DME" means 1,2-dimethoxyethane, "EtOAc" means ethyl acetate, "DCM" means dichloromethane and "BuLi" means n-butyl lithium.

A. PREPARATION OF THE INTERMEDIATES

Example A1 a) Sodium hydroxide (0.62 mol) was dissolved in methanol (100 mol) and the mixture was cooled till room temperature. 1-bromo-4-nitro-benzene (0.124 mol), followed by 3-chloro-benzeneacetonitrile (0.223 mol) were added dropwise, the temperature raised till 50° C. and the mixture was stirred at room temperature for one night. The mixture was poured into water and ice, the precipitate was filtered off, washed with water and extracted with DME and methanol. The organic layer was dried ($MgSO_4$), filtered off and evaporated till dryness. The residue was taken up in diethylether, filtered off and dried, yielding 13.2 g (34.8%) of 5-bromo-3-(3-chlorophenyl)-2,1-benzisoxazole, mp. 163° C. (intermediate 1).

b) $TiCl_3$ (1050 ml) was added at room temperature to a solution of intermediate (1) (0.386 mol) in THF (1350 ml) and the mixture was stirred at room temperature for 2 h. The mixture was poured into water and ice and extracted with DCM. The organic layer was decanted, washed with $K_2CO_3$ 10%, dried ($MgSO_4$), filtered off and evaporated, yielding 102 g (85%) of (2-amino-5-bromophenyl)(3-chlorophenyl)-methanone (intermediate 2).

c) A solution of intermediate (2) (0.328 mol) and acetic acid, anhydride (0.656 mol) in toluene (1200 ml) was stirred and refluxed for one night. The mixture was evaporated and the product was used without further purification, yielding 139 g (quant.) of N-[4-bromo-2-(3-chlorobenzoyl)phenyl]-acetamide (intermediate 3).

d) 2-methyl,2-propanol, potassium salt (1.635 mol) was added portionwise at room temperature to a solution of intermediate (3) (0.328 mol) in DME (1200 ml) and the mixture was stirred at room temperature for one night. The mixture was evaporated till dryness, the residue was poured into water and ice and decanted. The oily residue was taken up in DIPE, the precipitate was filtered off, washed with EtOAc, $CH_3CN$ and diethylether and dried, yielding 88.6 g (80.76%) of 6-bromo-4-(3-chlorophenyl)-2(1H)-quinolinone (intermediate 4).

e) A mixture of intermediate (4) (0.16 mol) in phosphoryl chloride (500 ml) was stirred and refluxed for one night. The mixture was evaporated till dryness, the residue was taken up in ice and water, alkalized with $NH_4OH$ and extracted with DCM. The organic layer was decanted, dried ($MgSO_4$), filtered off and evaporated, yielding 56 g (100%) 6-bromo-2-chloro-4-(3-chlorophenyl)quinoline, mp. 125° C. (intermediate 5).

f) $CH_3ONa$ 30%/$CH_3OH$ (96 ml) was added to a solution of intermediate (5)(0.16 mol) in methanol (500 ml) and the mixture was stirred and refluxed for one night. The mixture was evaporated till dryness, the residue was taken up in DCM, washed with water and decanted. The organic layer was dried ($MgSO_4$), filtered off and evaporated. The residue was taken up in diethylether and DIPE, the precipitate was filtered off and dried, yielding 48 g (86%) of 6-bromo-4-(3-chlorophenyl)-2-methoxyquinoline, mp. 124° C. (intermediate 6).

g) BuLi 1.6M in hexane (0232 mol) was added dropwise at –20° C. to a mixture of intermediate (6) (0.0223 mol) in THF (80 ml). The mixture was stirred at –20° C. for 30 min and added dropwise at –20° C. to a mixture of bis(1-methyl-1H-imidazol-5-yl)-methanone (0.0089 mol) in THF (20 ml). The mixture was stirred for 1 hour, hydrolyzed and extracted with EtOAc. The organic layer was separated, dried ($MgSO_4$), filtered and the solvent was evaporated till dryness. The residue was purified by column chromatography over silica gel (eluent: $CH_2Cl_2/CH_3OH/NH_4OH$ 90/10/0.5; 15–40 μm). The pure fractions were collected and the solvent was evaporated, yielding 0.20 g (5%) of 4-(3-chlorophenyl)-2-methoxy-α,α-bis(1-methyl-1H-imidazol-5-yl)-6-quinolinemethanol (intermediate 7).

Example A2 a) BuLi 1.6M in hexane (0.03 mol) was added dropwise at –78° C. under $N_2$ flow to a mixture of intermediate (6) (0.0287 mol) in THF (75 ml). The mixture was stirred at –78° C. for 15 min. A solution of 1-methyl-1H-imidazole-5-carboxaldehyde (0.03 mol) in THF (10 ml) was added quickly while the temperature was kept below 50° C. The mixture was allowed to warm to room temperature, hydrolyzed and extracted with DCM. The organic layer was separated, dried ($MgSO_4$), filtered and the solvent was evaporated. The residue (14.2 g) was purified by column chromatography over silica gel (eluent: $CH_2Cl_2/CH_3OH/NH_4OH$ 95/5/0.1; 20–45 μm). The pure fractions were collected and the solvent was evaporated. The residue was crystallized from 2-propanone and DIPE. The precipitate was filtered off and dried, yielding 5.3 g of 4-(3-chlorophenyl)-2-methoxy-α-(1-methyl-1H-imidazol-5-yl)-6-quinolinemethanol, mp. 205° C. (intermediate 8).

b) KMnO$_4$ (0.0182 mol) was added portionwise at room temperature to a mixture of intermediate (8) (0.018 mol) in 2-(2-methoxyethoxy)-N,N-bis[2-(2-methoxyethoxy)ethyl]-ethanamine (1 ml) and DCM (70 ml). The mixture was stirred at room temperature for 2 hours and then filtered over celite. The precipitate was washed with DCM. The organic solution was washed with water, dried (MgSO$_4$), filtered and the solvent was evaporated, yielding 6.8 g (100%) of [4-(3-chlorophenyl)-2-methoxy-6-quinolinyl](1-methyl-1H-imidazol-5-yl)-methanone (intermediate 9).

c) BuLi 1.6 M in hexane (0.0111 mol) was added dropwise at −70° C. under N$_2$ flow to a mixture of thiazole (0.0111 mol) in diethyl ether (30 ml). The mixture was stirred at −70° C. for 1 hour. A mixture of intermediate (9) (0.0074 mol) in THF (30 ml) was added dropwise. The mixture was stirred at −70° C. for 1 hour, hydrolyzed and extracted with EtOAc. The organic layer was separated, dried (MgSO$_4$), filtered and the solvent was evaporated till dryness. The residue (4 g) was purified by column chromatography over silica gel (eluent: CH$_2$Cl$_2$/CH$_3$OH/NH$_4$OH 97/3/0.1; 15–40 μm). The pure fractions were collected and the solvent was evaporated, yielding 3.1 g (91.1%) of 4-(3-chlorophenyl)-2-methoxy-α-(1-methyl-1H-imidazol-5-yl)-α-(2-thiazolyl)-6-quinolinemethanol (intermediate 10).

d) A mixture of intermediate (10)(0.0065 mol) in HCl 3N (100 ml) and THF (100 ml) was stirred and refluxed for 6 hours. The mixture was poured out on ice, alkalized with a concentrated NH$_4$OH solution and extracted with DCM. The organic layer was separated, dried (MgSO$_4$), filtered and the solvent was evaporated till dryness, yielding 3 g (>100%) of 4-(3-chlorophenyl)-6-[hydroxy(1-methyl-1H-imidazol-5-yl)-2-thiazolylmethyl]-2(1H)-quinolinone (intermediate 11).

Example A3 a) A mixture of sodium hydroxide (0.64 mol) in ethanol (300 ml) was stirred at room temperature for 15 min. 2-(4-nitrophenyl)-1,3-dioxolane (0.128 mol) was added portionwise. The mixture was stirred for 30 min. and 3-chlorobenzene acetonitrile (0.2304 mol) was added. The mixture was stirred at room temperature for 3 hours. Ice water was added. The precipitate was filtered off, washed with water and with ethanol and dried, yielding: 28.47 g (74%) of 3-(3-chlorophenyl)-5-(1,3-dioxolan-2-yl)-2,1-benzisoxazole (intermediate 12), mp. 160° C.

b) A mixture of intermediate (12) (0.0941 mol) in HCl 6N (200 ml) and methanol (100 ml) was stirred and refluxed for 6 hours, cooled and poured out on ice. The precipitate was filtered off, washed with diethyl ether and dried, yielding 21.8 g (90%) of 3-(3-chlorophenyl)-2,1-benzisoxazole-5-carboxaldehyde (intermediate 13), mp. 148° C.

c) BuLi (0.118 mol) was added dropwise at −70° C. under N$_2$ flow to a solution of 4-phenyl-thiazole (0.097 mol) in THF (205 ml). The mixture was stirred at −70° C. for 1 hour. A solution of intermediate (13) (0.0692 mol) in THF (205 ml) was added dropwise. The mixture was stirred at −70° C. for 2 hours, brought to −30° C. over a 90-min period, poured out into NH$_4$Cl 10% and extracted with DCM. The organic layer was separated, dried (MgSO$_4$) and the solvent was evaporated. The residue (39.5 g) was purified by column chromatography over silica gel (eluent: cyclohexane/EtOAc 80/20; 20–45 μm). The pure fractions were collected and the solvent was evaporated. A part (1.5 g) of the residue (18 g, 62%) was crystallized from 2-propanone. The precipitate was filtered off and dried, yielding 1.5 g (84%) of 3-(3-chlorophenyl)-α-(4-phenyl-2-thiazolyl)-2,1-benzisoxazole-5-methanol (intermediate 14), mp. 136° C.

d) A mixture of intermediate (14) (0.0656 mol) and MnO$_2$ (27.5 g) in 1,4-dioxane (275 ml) was stirred at 80° C. for 3 hours, then cooled to room temperature, filtered over celite and pasted up with CH$_2$Cl$_2$/CH$_3$OH. The solvent was evaporated till dryness, yielding 27.3 g (100%) of [3-(3-chlorophenyl)-2,1-benzisoxazol-5-yl](4-phenyl-2-thiazolyl)-methanone (intermediate 15).

e) TiCl$_3$ 15% in water (300 ml) was added slowly at room temperature to a mixture of intermediate (15) (0.0656 mol) in THF (500 ml). The mixture was stirred at room temperature overnight, then poured out into ice water, extracted with DCM and washed with K$_2$CO$_3$ 10%. The organic layer was separated, dried (MgSO$_4$), filtered and the solvent was evaporated till dryness, yielding 25.5 g (92.7%) of [4-amino-3-(3-chlorobenzoyl)phenyl](4-phenyl-2-thiazolyl)-methanone (intermediate 16).

f) A mixture of intermediate (16) (0.048 mol) in DCM (200 ml) was cooled on an ice bath. 3-chloro-3-oxo-propanoic acid, ethyl ester (0.105 mol) was added dropwise. The mixture was stirred at a low temperature for 30 min, then stirred and refluxed for 1 hour and poured out into water. The organic layer was separated, washed with K$_2$CO$_3$ 10%, dried (MgSO$_4$), filtered and the solvent was evaporated till dryness. The product was used without further purification, yielding (quant.) N-[2-(3-chlorobenzoyl)-4-[(4-phenyl-2-thiazolyl)carbonyl]phenyl]-3-oxo-β-alanine ethyl ester (intermediate 17).

g) A mixture of intermediate (17) (0.048 mol) in DME (250 ml) was cooled on an ice bath and 2-methyl-2-propanol, potassium salt (0.096 mol) was added portionwise. The mixture was stirred at a low temperature for 15 min, poured out into ice water and acidified with HCl 3N. The precipitate was filtered off, washed with water, pasted up with CH$_3$CN and diethyl ether, then dried, yielding 17.3 g (70%) of ethyl 4-(3-chlorophenyl)-1,2-dihydro-2-oxo-6-[(4-phenyl-2-thiazolyl)carbonyl]-3-quinolinecarboxylate (intermediate 18), mp 261° C.

h) A mixture of intermediate (18) (0.0336 mol) in methanol (100 ml) and THF (100 ml) was cooled on an ice bath. Sodium tetrahydroborate (0.0336 mol) was added portionwise. The mixture was stirred at a low temperature for 30 min, then poured out into ice water and extracted with DCM. The organic layer was separated, dried (MgSO$_4$), filtered and the solvent was evaporated till dryness. The residue was crystallized from 2-propanone/DIPE. The precipitate was filtered off and dried, yielding 14.2 g (81.6%) of ethyl 4-(3-chlorophenyl)-1,2-dihydro-6-[hydroxy(4-phenyl-2-thiazolyl)methyl]-2-oxo-3-quinolinecarboxylate (intermediate 19), mp. 127° C.

i) Thionyl chloride (30 ml) was added dropwise to a mixture of intermediate (19) (0.0245 mol) in DCM (150 ml), previously cooled on an ice bath. The mixture was stirred at a low temperature for 1 hour and at room temperature overnight. The solvent was evaporated till dryness. The product was used without further purification, yielding (quant.) of ethyl 4-(3-chlorophenyl)-6-[chloro(4-phenyl-2-thiazolyl)methyl]-1,2-dihydro-2-oxo-3-quinolinecarboxylate (intermediate 20).

Example A4 a) A mixture of intermediate (8) in HCl 3N (70 ml) was stirred at 80° C. for 16 hours, cooled, poured out on ice and basified with a concentrated NH$_4$OH solution. The precipitate was filtered off, washed with water and with diethyl ether, then dried, yielding 5.1 g (95%) of 4-(3-chlorophenyl)-6-[hydroxy(1-methyl-1H-imidazol-5-yl)methyl]-2(1H)-quinolinone (intermediate 21), mp. 186° C.

b) A mixture of intermediate (21) (0.0132 mol), iodomethane (0.0264 mol) and benzyltriethylammonium chloride (0.00132 mol) in THF (50 ml) and sodium hydroxide 10N (50 ml) was stirred at room temperature overnight. EtOAc was added. The mixture was decanted. The organic layer was dried, filtered and the solvent was evaporated. The residue (2.9 g) was purified by column chromatography over silica gel (eluent: $CH_2Cl_2/CH_3OH/NH_4OH$ 95/5/0.1; 15–40 µm). The pure fractions were collected and the solvent was evaporated. The residue was purified by column chromatography over silica gel (eluent: toluene/2-propanol/$NH_4OH$ 70/29/1; 15–40 µm). The pure fractions were collected and the solvent was evaporated. The residue was crystallized from diethyl ether. The precipitate was filtered off and dried, yielding 0.45 g of 4-(3-chlorophenyl)-6-[hydroxy(1-methyl-1H-imidazol-5-yl)methyl]-1-methyl-2(1H)-quinolinone, mp. 167° C. (intermediate 22).

c) A mixture of intermediate (22) (0.0026 mol) in thionyl chloride (10 ml) was stirred at 40° C. for 8 hours. The solvent was evaporated till dryness. This product was used without further purification, yielding 6-[chloro(1-methyl-1H-imidazol-5-yl)methyl]-4-(3-chlorophenyl)-1-methyl-2(1H)-quinolinone hydrochloride (intermediate 23).

Example A5 a) A mixture of (intermediate 6) (0.043 mol) in THF (150 ml) was cooled to –70° C. under $N_2$ flow. BuLi 1.6M in hexane (0.056 mol) was added dropwise. The mixture was stirred at –70° C. for 1 hour. A mixture of 3-furancarboxaldehyde (0.056 mol) in THF (60 ml) was added dropwise. The mixture was stirred at –70° C. for 30 min, hydrolized, extracted with EtOAc and decanted. The organic layer was dried ($MgSO_4$), filtered and the solvent was evaporated till dryness. The residue (20 g) was purified by column chromatography over silica gel (eluent: $CH_2Cl_2/CH_3OH$ 99/1; 20–45 µm). The pure fractions were collected and the solvent was evaporated, yielding 14 g (90%) of 4-(3-chlorophenyl)-α-(3-furanyl)-2-methoxy-6-quinolinemethanol (intermediate 24).

b) A mixture of (intermediate 24) (0.0382 mol) and $MnO_2$ (28 g) in trichloromethane (200 ml) was stirred and refluxed overnight. The mixture was cooled to room temperature, filtered over celite and the solvent was evaporated till dryness. The product was used without further purification, yielding 11.5 g (82.7%) of [4-(3-chlorophenyl)-2-methoxy-6-quinolinyl]-3-furanyl-methanone (intermediate 25).

c) A mixture of (intermediate 25) (0.0434 mol) in THF (160 ml) and HCl 3N (160 ml) was stirred and refluxed overnight. The mixture was poured out into ice water and alkalized with a concentrated $NH_4OH$ solution. The precipitate was filtered off, washed with water and dried, yielding 15 g (98.7%) of 4-(3-chlorophenyl)-6-(3-furanylcarbonyl)-2(1H)-quinolinone (intermediate 26), melting point >250° C.

d) A mixture of (intermediate 26) (0.04 mol) in DMF (200 ml) was cooled to 5° C. under $N_2$ flow. NaH 80% in oil (0.048 mol) was added portionwise. The mixture was stirred at 5° C. for 30 min. Then iodomethane (0.048 mol) was added dropwise. The mixture was stirred at 5° C. for 30 min, hydrolized and poured out into water. The precipitate was filtered off, washed with water and taken up in $CH_2Cl_2$. The organic layer was separated, dried ($MgSO_4$), filtered and the solvent was evaporated till dryness. The residue (15.5 g) was purified by column chromatography over silica gel (eluent: $CH_2Cl_2/EtOAc$ 85/15; 15–40 µm). The pure fractions were collected and the solvent was evaporated. The residue (13.3 g, 91.7%) was crystallized from $CH_3CN$ and DIPE. The precipitate was filtered off and dried, yielding 1.5 g (9.6%) of 4-(3-chlorophenyl)-6-(3-furanylcarbonyl)-1-methyl-2(1H)-quinolinone (intermediate 27), melting point 192° C.

Example A6 a) A mixture of intermediate 4 (0.045 mol), iodomethane (0.225 mol) and benzyltriethylammonium chloride (0.0045 mol) in NaOH (150 ml) and THF (150 ml) was stirred overnight. EtOAc was added. The mixture was washed with water. The organic layer was separated, dried ($MgSO_4$), filtered, and the solvent was evaporated till dryness. The residue was purified by column chromatography over silica gel (eluent: $CH_2Cl_2/EtOAc$; 95/5; 20–45 µm). The pure fractions were collected and the solvent was evaporated, yielding 13.5 g (86%) of 6-bromo-4-(3-chlorophenyl)-1-methyl-2(1H)-quinolinone (intermediate 28), melting point 182° C.

b) A mixture of (intermediate 28) (0.066 mol), 1-methyl-5-(tributylstannyl)-1H-imidazole (0.121 mol) and $Pd(PPh_3)_4$ (0.0066 mol) in triethylamine (23 ml) and dioxane (230 ml) was stirred at 90° C. overnight under a 5 bar pressure of carbon monoxide, then cooled, poured out into ice water and extracted with EtOAc. The mixture was filtered over celite and extracted with EtOAc. The organic layer was separated, dried ($MgSO_4$), filtered, and the solvent was evaporated, yielding fraction 1 (organic layer). Celite was washed with $CH_2Cl_2/CH_3OH$. The solvent was evaporated, yielding fraction 2. Fraction 2 was washed with diethyl ether, filtered off and dried under a vacuo, yielding 17.6 g (70%) of 4-(3-chlorophenyl)-1-methyl-6-[(1-methyl-1H-imidazol-5-yl)carbonyl]-2(1H)-quinolinone (intermediate 29).

B. PREPARATION OF THE FINAL COMPOUNDS

Example B1

A mixture of intermediate (7) (0.00141 mol) in HCl 3N (20 ml) and THF (5 ml) was stirred and refluxed overnight. The solvent was evaporated till dryness. The product was used without further purification, yielding 0.73 g (quant.) of 4-(3-chlorophenyl)-6-[hydroxybis(1-methyl-1H-imidazol-5-yl)methyl]-2(1H)-quinolinone hydrochloride (1:2).

Example B2

A mixture of 4-(3-chlorophenyl)-6-[hydroxybis(1-methyl-1H-imidazol-5-yl)methyl]-2(1H)-quinolinone hydrochloride (1:2) (obtained in Example B1) (0.00141 mol), iodomethane (0.00282 mol) and benzyltriethylammonium chloride (0.000141 mol) in sodium hydroxide (20 ml) and THF (20 ml) was stirred at room temperature overnight, then extracted with EtOAc and decanted. The organic layer was dried ($MgSO_4$), filtered and the solvent was evaporated till dryness. The residue (1.7 g) was purified by column chromatography over silica gel (eluent: $CH_2Cl_2/CH_3OH/NH_4OH$ 95/5/0.5; 15–40 µm). The pure fractions were collected and the solvent was evaporated. The residue was dissolved in 2-propanone and converted into the ethanedioic acid salt (1:2). The precipitate was filtered off and dried, yielding 0.16 g (16.5%) of 4-(3-chlorophenyl)-6-[hydroxybis(1-methyl-1H-imidazol-5-yl)methyl]-1-methyl-2(1H)-quinolinone ethanedioate (1:2) hydrate (1:3), mp=154° C.

Example B3

NaH 80% in oil (0.008 mol) was added under $N_2$ flow to a mixture of intermediate (11) (0.0067 mol) in N,N-dimethylformamide (30 ml), while cooling on ice. The mixture was stirred at this temperature for 1 hour. Iodomethane (0.008 mol) was added dropwise. The mixture was stirred at room temperature for 1 hour, hydrolyzed and extracted with EtOAc. The organic layer was separated, dried ($MgSO_4$), filtered and the solvent was evaporated till dryness. The residue (3 g) was purified by column chromatography over silica gel (eluent: $CH_2Cl_2/CH_3OH/NH_4OH$ 95/5/0.1; 15–40 μm). Two pure fractions were collected and the solvent was evaporated, yielding 0.8 g F1 and 1.2 g F2 (38.7%). F1 was dissolved in 2:-propanone and converted into the ethanedioic acid salt (1:1). The precipitate was filtered off and dried, yielding 0.7 g (17.9%) of (±)-4-(3-chlorophenyl)-6-[methoxy(1-methyl-1H-imidazol-5-yl)-2-thiazolylmethyl]-1-methyl-2(1H)-quinolinone ethanedioate (1:1) monohydrate mp. 246° C.

F2 was crystallized from $CH_3CN$, 2-propanone and DIPE. The precipitate was filtered off and dried, yielding 0.75 g (24%) of (±)-4-(3-chlorophenyl)-6-[hydroxy(1-methyl-1H-imidazol-5-yl)-2-thiazolylmethyl]-1-methyl-2(1H)-quinolinone, mp. 246° C.

Example B4 a) A mixture of intermediate (20) (0.0245 mol), 2-phenyl-1H-imidazole (0.0368 mol) and $K_2CO_3$ (0.0735 mol) in acetonitrile (150n) was stirred at 60° C. The solvent was evaporated till dryness. The residue was taken up in DCM and water. The organic layer was separated, dried ($MgSO_4$), filtered and the solvent was evaporated till dryness. The residue was purified by column chromatography over silica gel (eluent: $CH_2Cl_2/CH_3OH/NH_4OH$ 97/3/0.1; 15–40 μm). The pure fractions were collected and the solvent was evaporated, yielding 0.8 g (5.1%) of ethyl 4-(3-chlorophenyl)-1,2-dihydro-2-oxo-6-[(2-phenyl-1H-imidazol-1-yl)(4-phenyl-2-thiazolyl)methyl]-3-quinolinecarboxylate.

b) A solution of ethyl 4-(3-chlorophenyl)-1,2-dihydro-2-oxo-6-[(2-phenyl-1H-imidazol-1-yl)(4-phenyl-2-thiazolyl)methyl]-3-quinolinecarboxylate, obtained in stage a) (0.00124 mol) in THF (15 ml) was added dropwise at 5° C. under $N_2$ flow to a mixture of $LiAlH_4$ (0.0049 mol) in THF (10 ml). The mixture was stirred at 5° C. for 1 hour and hydrolyzed. EtOAc was added. The mixture was filtered over celite and the filtrate was decanted. The organic layer was dried ($MgSO_4$), filtered and the solvent was evaporated till dryness. The residue (0.7 g) was purified by column chromatography over silica gel (eluent: $CH_2Cl_2/CH_3OH$ 95/5; 15–40 μm). The pure fractions were collected and the solvent was evaporated. The residue (0.5 g) was converted into the ethanedioic acid salt (1:1) in 2-propanone/$CH_3CN$/DIPE. The precipitate was filtered off and dried, yielding: 0.43 g (50%) of 4-(3-chlorophenyl)-3-(hydroxymethyl)-6-[(2-phenyl-1H-imidazol-1-yl)(4-phenyl-2-thiazolyl)methyl]-2(1H)-quinolinone ethanedioate, mp. 149° C.

Example B5

Benzimidazole (0.0078 mol) was added to a mixture of intermediate (23) (0.0026 mol) in acetonitrile (20 ml). The mixture was stirred and refluxed for 6 hours, taken up in $CH_2Cl_2/H_2O$. The organic layer was separated, dried ($MgSO_4$), filtered and the solvent was evaporated till dryness. The residue (0.84 g) was purified by column chromatography over silica gel (eluent: toluene/iPrOH/$NH_4OH$ 65/25/0.5 to 50/50/2; 15–40 μm). The pure fractions were collected and the solvent was evaporated. The residue (0.6 g, 48%) was crystallized from $CH_3CN$. The precipitate was filtered off and dried, yielding 0.58 g (46%) of 6-[(1H-benzimidazol-1-yl(1-methyl-1H-imidazol-5-yl)methyl]-4-(3-chlorophenyl)-1-methyl-2(1H)-quinolinone, mp. >260° C.

Example B6

BuLi 1.6M (20.6 ml) was added dropwise at −70° C. under $N_2$ flow to a mixture of 1-methyl-1H-imidazole (0.033 mol) in THF (60 ml). The mixture was stirred at −70° C. for 30 min. chlorotriethyl-silane (0.033 mol) was added. The mixture was brought slowly to 10° C. and cooled again to −70° C. BuLi 1.6M (20.6 ml) was added dropwise. The mixture was stirred at −70° C. for 1 hour, brought to −15° C. and cooled again to −70° C. A suspension of (intermediate 27) (0.022 mol) in THF (80 ml) was added dropwise. The mixture was stirred at −70° C. for 30 min, then brought to room temperature, hydrolized, extracted with EtOAc and decanted. The organic layer was dried ($MgSO_4$), filtered and the solvent was evaporated till dryness. The residue (13 g) was purified by column chromatography over silica gel (eluent: $CH_2Cl_2/CH_3OH/NH_4OH$ 95/5/0.2; 20–45 μm). Two pure fractions were collected and their solvents were evaporated. The residue was crystallized from $CH_3CN$ and diethyl ether. The precipitate was filtered off and dried. Yielding: 1.2 g (12.2%) of (±)-4-(3-chlorophenyl)-6-[3-furanylhydroxy(1-methyl-1H-imidazol-5-yl)methyl]-1-methyl-2(1H)-quinolinone, melting point 248° C.

Example B7

A mixture of 1-methyl-1H-imidazole (0.0054 mol) in THF (10 ml) was cooled to −70° C. BuLi 1.6M (3.4 ml) was added dropwise and the mixture stood at −70° C. for 30 min. Chlorotriethylsilane (0.0054 mol) was added. The mixture was allowed to warm to 10° C. and then cooled to −70° C. BuLi 1.6M (3.4 ml) was added dropwise. The mixture stood at −70° C. for 1 hour, brought quickly to −15° C. and cooled to −70° C. THF (20 ml) and then intermediate 29) (0.0045 mol) were added. The mixture was allowed to warm to room temperature, stirred at room temperature overnight, stirred and refluxed for 24 hours, then hydrolized and extracted with DCM. The organic layer was separated, dried ($MgSO_4$), filtered and the solvent was evaporated till dryness. The residue (2.7 g) was purified by column chromatography over silica gel (eluent: $CH_2Cl_2/CH_3OH/NH_4OH$ 95/5/0.5; 15–40 μm). The pure fractions were collected and the solvent was evaporated. The residue was crystallized from 2-propanone/DIPE. The precipitate was filtered off and dried, yielding 0.6 g (28%) of 4-(3-chlorophenyl)-6-[hydroxy(1-methyl-1H-imidazol-2-yl)(1-methyl-1H-imidazol-5-yl)methyl]-1-methyl-2(1H)-quinolinone, melting point 130° C.

Example B8 a) BuLi 1.6M (20.6 ml) was added dropwise at −70° C. under $N_2$ flow to a mixture of 1-methyl-1H-imidazole (0.033 mol) in THF (60 ml). The mixture was stirred at −70° C. for 30 min. chlorotriethyl-silane (0.033 mol) was added. The mixture was brought slowly to 10° C. and cooled again to −70° C. BuLi 1.6M (20.6 ml) was added dropwise. The mixture was stirred at −70° C. for 1 hour, brought to −15° C. and cooled again to −70° C. A suspension of intermediate 27 (0.022 mol) in THF (80 ml) was added dropwise. The mixture was stirred at −70° C. for 30 min, then brought to room temperature, hydrolized, extracted with EtOAc and decanted. The organic layer was dried (MgSO$_4$), filtered and the solvent was evaporated till dryness. The residue (13 g) was purified by column chromatography over silica gel (eluent: CH$_2$Cl$_2$/CH$_3$OH/NH$_4$OH 95/5/0.2; 20–45 µm). One pure fraction was collected and the solvent evaporated. The residue was crystallized from CH$_3$CN and diethyl ether. The precipitate was filtered off and dried, yielding 1.2 g (12.2%) of 4-(3-chlorophenyl)-6-[3-furanylhydroxy(1-methyl-1H-imidazol-5-yl)methyl]-1-methyl-2(1H)-quinolinone, melting point 248° C.

b) 4-(3-chlorophenyl)-6-[3-furanylhydroxy(1-methyl-1H-imidazol-5-yl)methyl]-1-methyl-2(1H)-quinolinone (obtained in stage a) (0.0045 mol) was added to thionyl chloride (30 ml) at 5° C. The mixture was stirred at room temperature for 2 hours. The solvent was evaporated till dryness. The product was used without further purification, yielding (quant.) of 6-[chloro-3-furanyl(1-methyl-1H-imidazol-5-yl)methyl]-4-(3-chlorophenyl)-1-methyl-2(1H)-quinolinone.

c) A mixture of 6-[chloro-3-furanyl(1-methyl-1H-imidazol-5-yl)methyl]-4-(3-chlorophenyl)-1-methyl-2(1H)-quinolinone (obtained in stage b) (0.0045 mol) in THF (30 ml) was cooled to 5° C. 2-Propanol-NH$_3$ saturated (30 ml) was added dropwise quickly. The mixture was stirred at room temperature for 1 hour. The solvent was evaporated till dryness. The residue was taken up in DCM and water and the mixture was decanted. The organic layer was dried (MgSO$_4$), filtered and the solvent was evaporated till dryness. The residue (2.2 g) was purified by column chromatography over silica gel (eluent: toluene/2-propanol/NH$_4$OH 85/13/1; 15–40 µm). The pure fractions were collected and the solvent was evaporated. The residue was crystallized from CH$_3$CN and DIPE. The precipitate was filtered off and dried, yielding 0.55 g (27.5%) of (±)-6-[amino-3-furanyl(1-methyl-1H-imidazol-5-yl)methyl]-4-(3-chlorophenyl)-1-methyl-2(1H)-quinolinone, melting point 197° C.

The following compounds were prepared analogous to the one of the above examples (the example number analogous to which they were prepared is indicated between square brackets after the compound number). Mass spectral data (ms) is given for MH$^+$ peaks, determined by electron spray ionisation (ESI).

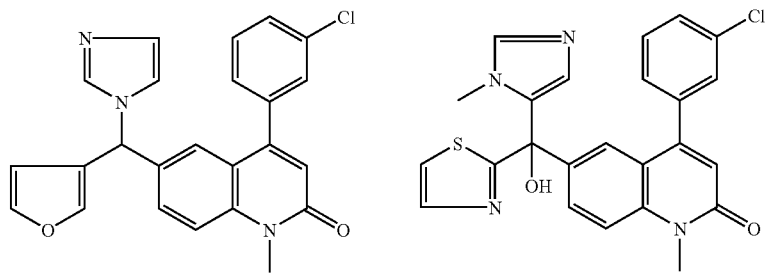

ethanedioate; [B5],
mp. 195° C.

[B3], MS(MH+): 462, 464

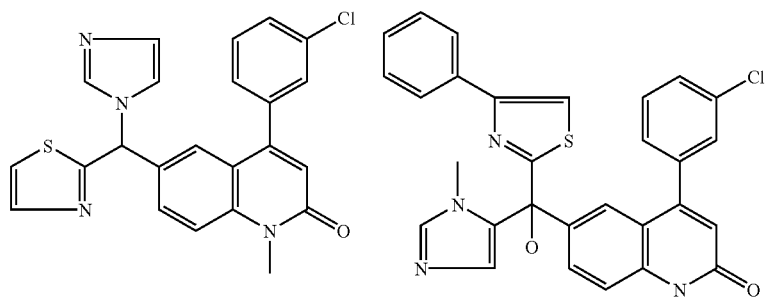

[B5], mp. 86° C.

[B3], mp > 260° C.

-continued
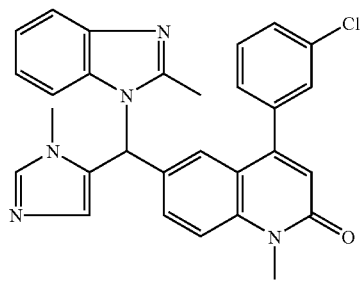
[B5], MS: 494, 496
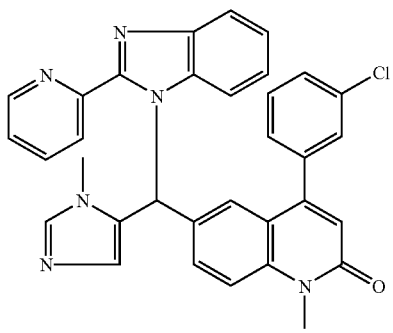
[B5], MS: 557, 559
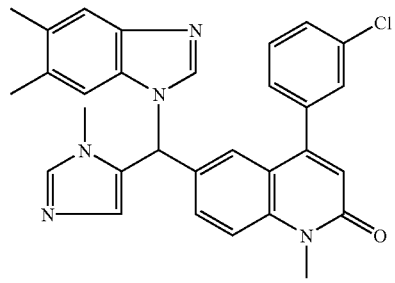
[B5], MS: 508, 510
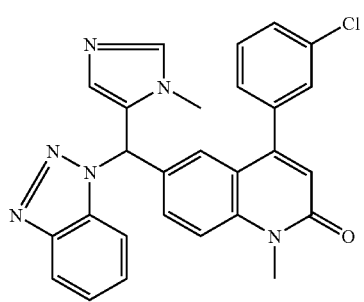
[B5]; MS(MH$^+$): 480, 482
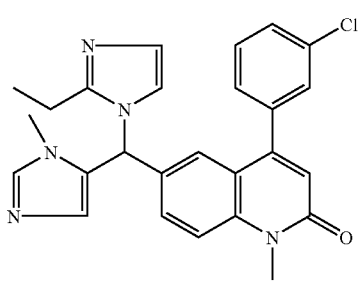
[B5]; MS(MH$^+$): 457, 459
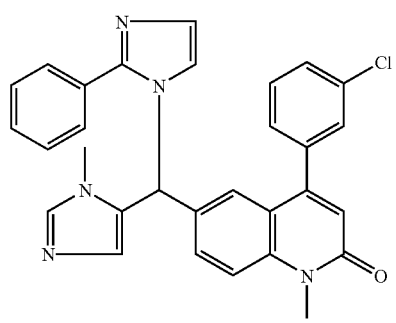
[B5]; MS(MH$^+$): 505, 507
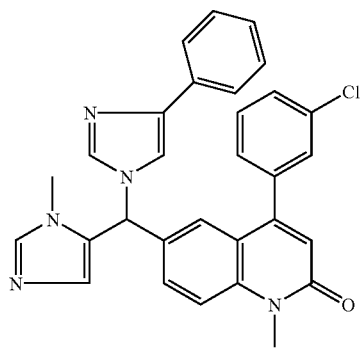
[B5]; MS(MH$^+$): 505, 507
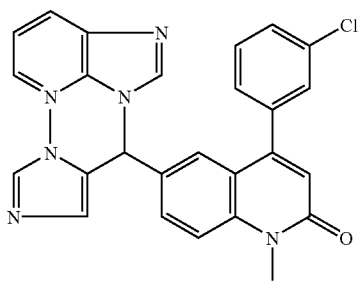
[B5]; MS(MH$^+$): 480, 482
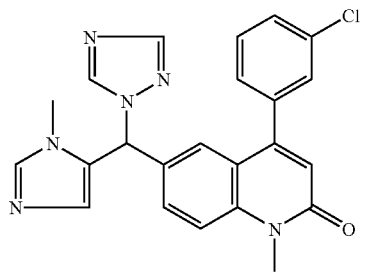
[B5]; MS(MH$^+$): 430, 432
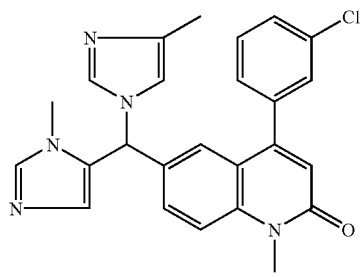
[B5]; MS(MH$^+$): 443, 445

C. PHARMACOLOGICAL EXAMPLE

Example C.1

"In Vitro Assay for Inhibition of Farnesyl Protein Transferase"

An in vitro assay for inhibition of farnesyl transferase was performed essentially as described in WO 98/40383, pages 33–34.

Example C.2

"Ras-Transformed Cell Phenotype Reversion Assay"

The ras-transformed cell phenotype reversion assay was performed essentially as described in WO 98/40383, pages 34–36.

Example C.3

"Farnesyl Protein Transferase Inhibitor Secondary Tumor Model"

The farnesyl protein transferase inhibitor secondary tumor model was used as described in WO 98/40383, page 37.

D. COMPOSITION EXAMPLE

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I):

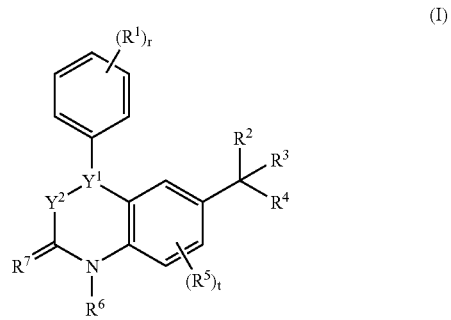

or a pharmaceutically acceptable salt or N-oxide or stereochemically isomeric form thereof, wherein r is 0, 1, 2, 3, 4, or 5;
t is 0, 1, 2, or 3;
$>Y^1-Y^2-$ is a trivalent radical of formula $$>C=CR^9- \quad (y\text{-}2);$$

wherein $R^9$ is hydrogen, halo, cyano, $C_{1-6}$alkyl, hydroxyC$_{1-6}$alkyl, $C_{1-6}$alkyloxyC$_{1-6}$alkyl, $-(CR^{20}R^{21})_p-C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alkyloxycarbonyl, aryl, or a group of formula $-NR^{22}R^{23}$, $-C_{1-6}$alkyl-NR$^{22}$R$^{23}$, $-C_{2-6}$alkenyl-NR$^{22}$R$^{23}$, $-CONR^{22}R^{23}$, or $-NR^{22}-C_{1-6}$alkyl-NR$^{22}$R$^{23}$;

p is 0 to 5;
$R^{20}$ and $R^{21}$ are independently hydrogen or $C_{1-6}$ alkyl and are independently defined for each iteration of p in excess of 1;
$R^{22}$ and $R^{23}$ are independently hydrogen, $C_{1-6}$ alkyl, or $-(CR^{20}R^{21})_p-C_{3-10}$cycloalkyl;

$R^1$ is azido, hydroxy, halo, cyano, nitro, $C_{1-6}$alkyl, $-(CR^{20}R^{21})_p-C_{3-10}$cycloalkyl, cyanoC$_{1-6}$alkyl, hydroxyC$_{1-6}$alkyl, $C_{1-6}$alkyloxyC$_{1-6}$alkyl, hydroxycarbonylC$_{1-6}$alkyloxyC$_{1-6}$alkyl, $R^{24}$SC$_{1-6}$alkyl, trihalomethyl, arylC$_{1-6}$alkyl, Het$^2$C$_{1-6}$alkyl, $-C_{1-6}$alkyl-NR$^{22}$R$^{23}$, $-C_{1-6}$alkylNR$^{22}$C$_{1-6}$alkyl-NR$^{22}$R$^{23}$, $-C_{1-6}$alkylNR$^{22}$COC$_{1-6}$alkyl, $-C_{1-6}$alkylNR$^{22}$COAlkAr$^2$, $-C_{1-6}$alkylNR$^{22}$COAr$^2$, $C_{1-6}$alkylsulphonylaminoC$_{1-6}$ alkyl, $C_{1-6}$alkyloxy, hydroxyC$_{1-6}$alkyloxy, $C_{1-6}$alkyloxyC$_{1-6}$alkyloxy, $-OC_{1-6}$alkyl-NR$^{22}$R$^{23}$, trihalomethoxy, arylC$_{1-6}$alkyloxy, Het$^2$C$_{1-6}$alkyloxy, $C_{1-6}$alkylthio, $C_{2-6}$alkenyl, cyanoC$_{2-6}$alkenyl, $-C_{2-6}$alkenyl-NR$^{22}$R$^{23}$, hydroxycarbonylC$_{2-6}$alkenyl, $C_{1-6}$alkyloxycarbonylC$_{2-6}$alkenyl, $C_{2-6}$alkynyl, $-CHO$, $C_{1-6}$alkylcarbonyl, hydroxyC$_{1-6}$alkylcarbonyl, hydroxycarbonyl, $C_{1-6}$alkyloxycarbonyl, $-CONR^{22}R^{23}$, $-CONR^{22}-C_{1-6}$alkyl-NR$^{22}$R$^{23}$, $-CONR^{22}-C_{1-6}$alkyl-Het$^2$, $-CONR^{22}-C_{1-6}$alkyl-Ar$^2$, $-CONR^{22}-O-C_{1-6}$alkyl, $-CONR^{22}-C_{1-6}$alkenyl, $-NR^{22}R^{23}$, $-OC(O)R^{24}$, $-CR^{24}=NR^{25}$, $-CR^{24}=N-OR^{25}$, $-NR^{24}C(O)NR^{22}R^{23}$, $-NR^{24}SO_2R^{25}$, $-NR^{24}C(O)R^{25}$, $-S(O)_{0-2}R^{24}$, $-SO_2NR^{24}R^{25}$, $-C(NR^{26}R^{27})=NR^{28}$, $-Sn(R^{24})_3$, $-SiR^{24}R^{24}R^{25}$, $-B(OR^{24})_2$, $-P(O)OR^{24}OR^{25}$, aryloxy, or a group of formula -Z, $-CO$-Z, or $-CO$-NR$^y$-Z in which $R^y$ is hydrogen or $C_{1-4}$alkyl and Z is phenyl the phenyl ring being optionally substituted by one or two substituents each independently selected from halo, cyano, hydroxycarbonyl, aminocarbonyl, $C_{1-6}$alkylthio, hydroxy, —$NR^{22}R^{23}$, $C_{1-6}$alkylsulphonylamino, $C_{1-6}$alkyl, halo$C_{1-6}$alkyl, $C_{1-6}$alkyloxy, or phenyl; or two $R^1$ substituents adjacent to one another on the phenyl ring may form together a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6)

$R^{24}$ and $R^{25}$ are independently hydrogen, $C_{1-6}$ alkyl, —(CR$_{20}$R$_{21}$)p-C$_{3-10}$cycloalkyl, or arylC$_{1-6}$alkyl;

$R^{26}$, $R^{27}$, and $R^{28}$ are independently hydrogen and $C_{1-6}$alkyl or C(O)C$_{1-6}$alkyl;

$R^2$ is imidazolyl;

$R^3$ is hydrogen, —O—$R^{10}$, or —$NR^{11}R^{12}$; wherein $R^{10}$ is hydrogen, $C_{1-6}$alkyl, —(CR$^{20}$R$^{21}$)$_p$—C$_{3-10}$cycloalkyl, arylC$_{1-6}$alkyl, C$_{2-6}$alkenyl, C$_{2-6}$alkynyl, $C_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula -Alk-OR$^{13}$, or -Alk-NR$^{14}$R$^{15}$;

$R^{11}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, aryl, or arylC$_{1-6}$alkyl;

$R^{12}$ is hydrogen, hydroxy, $C_{1-6}$alkyl, —(CR$^{20}$R$^{21}$)$_p$—C$_{3-10}$cycloalkyl, C$_{16}$alkylcarbonylC$_{1-6}$alkyl, arylC$_{1-6}$ alkyl, C$_{2-6}$alkenyl, C$_{2-6}$alkynyl, aryl, $C_{1-6}$alkyloxy, a group of formula —NR$^{22}$R$^{23}$, C$_{1-6}$alkylcarbonylamino, C$_{16}$alkylcarbonyl, haloC$_{1-6}$ alkylcarbonyl, arylC$_{1-6}$alkylcarbonyl, arylcarbonyl, C$_{1-6}$alkyloxycarbonyl, C$_{C16}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl and C$_{1-6}$alkyloxycarbonyl substituents; aminocarbonylcarbonyl, mono- or di(C$_{1-}$ di(C$_{1-6}$alkyl)aminoC$_{1-6}$alkylcarbonyl, or a radical of formula -Alk-OR$^{13}$ or Alk-NR$^{14}$R$^{15}$; wherein Alk is C$_{1-6}$alkanediyl;

$R^{13}$ is hydrogen, $C_{1-6}$alkyl, —(CR$^{20}$R$^{21}$)$_p$—C$_{3-10}$cycloalkyl, C$_{2-6}$alkenyl, C$_{26}$alkynyl, C$_{1-6}$alkylcarbonyl, hydroxyC$_{1-6}$alkyl, aryl, or arylC$_{1-6}$alkyl;

$R^{14}$ is hydrogen, $C_{1-6}$alkyl, —(CR$^{20}$R$^{21}$)$_p$—C$_{3-10}$cycloalkyl, C$_{2-6}$alkenyl, C$_{26}$alkynyl, aryl, or arylC$_{1-6}$alkyl;

$R^{15}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, aryl, or arylC$_{1-6}$alkyl;

$R^4$ is a radical of formula

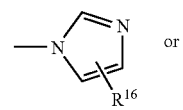
(c-1)

or

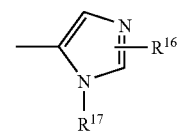
(c-2)

wherein $R^{16}$ is hydrogen, halo, $C_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, hydroxycarbonyl, C$_{1-6}$alkyloxycarbonyl, or aryl;

$R^{17}$ is hydrogen, $C_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylC$_{1-6}$alkyl, C$_{1-6}$alkyloxycarbonylC$_{1-6}$alkyl, mono- or di (C$_{1-6}$alkyl)aminosulphonyl, or —C$_{1-6}$alkylP(O)OR$^{24}$OR$^{25}$;

$R^5$ is cyano, hydroxy, halo, $C_{1-6}$alkyl, —(CR$^{20}$R$^{21}$)$_p$—C$_{3-10}$cycloalkyl, C$_{2-6}$alkenyl, C$_{26}$alkynyl, C$_{1-6}$alkyloxy, arylC$_{1-6}$alkyloxy, Het$^2$C$_{1-6}$alkyloxy, hydroxycarbonyl, C$_{1-6}$alkyloxycarbonyl, or a group of formula —NR$^{22}$R$^{23}$ or —CONR$^{22}$R$^{23}$;

$R^6$ is hydrogen;

$R^7$ is oxygen or sulphur;

and Ar is phenyl.

2. A compound of claim 1 wherein r is 0, 1, or 2;

t is 0 or 1;

>Y$^1$–Y$^2$— is a trivalent radical of formula

>C=CR$^9$— (y-2)

wherein $R^9$ is hydrogen, cyano, halo, $C_{1-6}$alkyl, hydroxyC$_{1-6}$alkyl, hydroxycarbonyl, or aminocarbonyl;

$R^1$ is halo, $C_{1-6}$alkyl, —(CR$^{20}$R$^{21}$)$_p$—C$_{3-10}$cycloalkyl, trihalomethyl, trihalomethoxy, C$_{2-6}$alkenyl, hydroxycarbonylC$_{2-6}$alkenyl, C$_{2-6}$alkynyl, C$_{16}$alkyloxy, hydroxyC$_{1-6}$alkyloxy, aminoC$_{1-6}$alkyloxy, C$_{1-6}$alkylthio, hydroxycarbonyl, C$_{1-6}$alkyloxycarbonyl, —CONR$^{22}$R$^{23}$, or —CH=NOR$^{25}$; or two R$^1$ substituents adjacent to one another on the phenyl ring may independently form together a bivalent radical of formula —O—CH$_2$—O— (a-1)

or

—O—CH$_2$—CH$_2$—O— (a-2)

$R^2$ is imidazolyl; $R^3$ is hydrogen, —O—$R^{10}$, or —NR$^{11}$R$^{12}$;

wherein $R^{10}$ is hydrogen, $C_{1-6}$alkyl, or —(CR$^{20}$R$^{21}$)$_p$—C$_{3-10}$cycloalkyl, or a group of formula -Alk-OR$^{13}$, or -Alk-NR$^{14}$R$^{15}$;

$R^{11}$ is hydrogen or $C_{1-6}$alkyl;
$R^{12}$ is hydrogen, hydroxy, $C_{1-6}$alkyl, —$(CR^{20}R^{21})_p$—$C_{3-10}$cycloalkyl, $C_{16}$alkyloxy, $C_{1-6}$alkylcarbonyl, aminocarbonyl, or a radical of formula Alk-OR$^{13}$, or Alk-NR$^{14}$R$^{15}$;
wherein Alk is $C_{1-6}$alkanediyl;
$R^{13}$ is hydrogen, $C_{1-6}$alkyl, or —$(CR^{20}R^{21})_p$—$C_{3-10}$cycloalkyl;
$R^{14}$ is hydrogen, $C_{1-6}$alkyl, or —$(CR^{20}R^{21})_p$—$C_{3-10}$cycloalkyl;
$R^{15}$ is hydrogen or $C_{1-6}$alkyl;
$R^4$ is a radical of formula (c-2) wherein $R^{16}$ is hydrogen, halo, or $C_{1-6}$alkyl
$R^{17}$ is hydrogen, $C_{1-6}$alkyl, —$(CR^{20}R^{21})_p$—$C_{3-10}$cycloalkyl, $C_{1-6}$alkyloxy$C_{1-6}$alkyl, or trifluoromethyl;
$R^5$ is cyano, halo, $C_{1-6}$alkyl, $C_{2-6}$alkynyl, $C_{1-6}$alkyloxy, or $C_{1-6}$alkyloxycarbonyl:
$R^6$ is hydrogen, $C_{1-6}$alkyl, —$C_{1-6}$alkylCO$_2$R$^{24}$, $C_{1-6}$alkyl-C(O)NR$^{22}$R$^{23}$, or Alk-Ar$^2$; and
$R^7$ is oxygen.

3. A compound of claim 1 wherein
>$Y^1$–$Y^2$— is a trivalent radical of formula (y-2), wherein $R^9$ is hydrogen, halo, $C_{1-4}$alkyl, hydroxycarbonyl, or $C_{1-4}$alkyloxycarbonyl;
r is 0, 1, or 2;
t is 0;
$R^1$ is halo, $C_{1-6}$alkyl or two $R^1$ substituents ortho to one another on the phenyl ring may independently form together a bivalent radical of formula (a-1);
$R^2$ is imidazolyl;
$R^3$ is —OR$^{10}$ or NHR$^{12}$; wherein
$R^{10}$ is hydrogen or a group of formula -Alk-OH;
$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl; and Alk is $C_{1-6}$alkanediyl;
$R^4$ is a group of formula (c-2) wherein
$R^{16}$ is hydrogen, halo, or mono- or di($C_{1-4}$alkyl)amino;
$R^{17}$ is hydrogen or $C_{1-6}$alkyl;
$R^6$ is —$(CR^{20}R^{21})_p$—$C_{3-10}$cycloalkyl, —$C_{1-6}$alkylCO$_2$R$^{24}$, aminocarbonyl$C_{1-6}$alkyl, -Alk-Ar$^2$ or $C_{1-6}$alkyl;
$R^7$ is oxygen; and
aryl is phenyl.

4. A compound of claim 1 wherein
>$Y^1$–$Y^2$ is a trivalent radical of formula (y-2);
r is 0 or 1;
t is 0;
$R^1$ is halo or $C_{(1-4)}$alkyl or forms a bivalent radical of formula (a-1);
$R^2$ is imidazolyl;
$R^4$ is a radical of formula (c-2), wherein
$R^6$ is $C_{1-6}$alkyl, —CH$_2$—$C_{3-10}$cycloalkyl, —$C_{16}$alkylCO$_2$R$^{24}$, (wherein R$^{24}$ is hydrogen or ethyl), aminocarbonyl$C_{1-6}$alkyl, or -Alk-Ar$^2$;
$R^7$ is oxygen;
$R^{10}$ is hydrogen or -Alk-OH;
$R^{11}$ is hydrogen; and
$R^{12}$ is hydrogen or $C_1.C_{1-6}$alkylcarbonyl.

5. A compound of claim 1 wherein
>$Y^1$–$Y^2$ is a trivalent radical of formula (y-2);
r is 1;
t is 0;
$R^1$ is halo;
$R^2$ is a imidazol-1-yl, group optionally substituted by halo, cyano, or $C_{1-6}$alkyl;
$R^3$ is a radical of formula (b-1) or (b-3);
$R^4$ is a radical of formula (c-2);
$R^6$ is $C_{16}$alkyl, —CH$_2$—$C_{3-10}$cycloalkyl, or -alkylAr$^2$;
$R^7$ is oxygen;
$R^9$, $R^{10}$, and $R^{11}$ is each hydrogen; and
$R^{12}$ is hydrogen or hydroxy.

6. A compound of claim 1 selected from the group consisting of:
4-(3-chlorophenyl)-1-methyl-6-[(1-methyl-1H-imidazol-5-yl)(2-phenyl-1H-imidazol-1yl)methyl]-2(1H)-quinolinone,
4-(3-chlorophenyl)-6-[(2-ethyl-1H-imidazol-1-yl)(1-methyl-1H-imidazol-5-yl)methyl]-1-methyl-2(1H)-quinolinone, and
4-(3-chlorophenyl)-1-methyl-6-[(1-methyl-1H-imidazol-5-yl)(4-methyl-1H-imidazol-1-yl)methyl]-2(1H)-quinolinone,
and their pharmaceutically acceptable salts.

7. A pharmaceutical composition comprising a pharmaceutically acceptable carrier, and an active ingredient comprising a therapeutically effective amount of a compound of claim 1.

8. A pharmaceutical composition comprising a pharmaceutically acceptable carrier, and an active ingredient comprising a therapeutically effective amount of a compound of claim 2.

9. A pharmaceutical composition comprising a pharmaceutically acceptable carrier, and an active ingredient comprising a therapeutically effective amount of a compound of claim 3.

10. A pharmaceutical composition comprising a pharmaceutically acceptable carrier, and an active ingredient comprising a therapeutically effective amount of a compound of claim 4.

11. A pharmaceutical composition comprising a pharmaceutically acceptable carrier, and an active ingredient comprising a therapeutically effective amount of a compound of claim 5.

12. A pharmaceutical composition comprising a pharmaceutically acceptable carrier, and an active ingredient comprising a therapeutically effective amount of a compound of claim 6.

* * * * *